US012716076B2

(12) United States Patent
Nishida et al.

(10) Patent No.: US 12,716,076 B2
(45) Date of Patent: Aug. 25, 2026

(54) METHOD FOR INCREASING MUTATION INTRODUCTION EFFICIENCY IN GENOME SEQUENCE MODIFICATION TECHNIQUE, AND MOLECULAR COMPLEX TO BE USED THEREFOR

(71) Applicant: NATIONAL UNIVERSITY CORPORATION KOBE UNIVERSITY, Kobe (JP)

(72) Inventors: Keiji Nishida, Kobe (JP); Akihiko Kondo, Kobe (JP); Takayuki Arazoe, Kobe (JP); Zenpei Shimatani, Kobe (JP)

(73) Assignee: NATIONAL UNIVERSITY CORPORATION KOBE UNIVERSITY, Kobe (JP)

( * ) Notice: Subject to any disclaimer, the term of this patent is extended or adjusted under 35 U.S.C. 154(b) by 452 days.

(21) Appl. No.: 16/094,587

(22) PCT Filed: Apr. 21, 2017

(86) PCT No.: PCT/JP2017/016105
§ 371 (c)(1),
(2) Date: Oct. 18, 2018

(87) PCT Pub. No.: WO2017/183724
PCT Pub. Date: Oct. 26, 2017

(65) Prior Publication Data

US 2020/0377910 A1 Dec. 3, 2020

(30) Foreign Application Priority Data

Apr. 21, 2016 (JP) ................................ 2016-085631

(51) Int. Cl.
*C12N 15/90* (2006.01)
*C12N 9/22* (2006.01)
*C12N 9/78* (2006.01)
*C12N 15/11* (2006.01)

(52) U.S. Cl.
CPC ............... *C12N 15/90* (2013.01); *C12N 9/22* (2013.01); *C12N 9/78* (2013.01); *C12N 15/11* (2013.01); *C12N 2310/20* (2017.05); *C12Y 305/04005* (2013.01)

(58) Field of Classification Search
CPC .... C12Y 305/04005; C12N 15/90–907; C12N 9/22; C12N 2310/20; C12N 9/78; C12N 15/102
See application file for complete search history.

(56) References Cited

U.S. PATENT DOCUMENTS

| | | | | |
|---|---|---|---|---|
| 6,117,680 A | | 9/2000 | Natesan et al. | |
| 8,697,359 B1 | | 4/2014 | Zhang | |
| 8,772,008 B2 * | | 7/2014 | Doyon .................... | C12N 9/22 435/196 |
| 10,655,123 B2 * | | 5/2020 | Nishida .................... | C12N 9/22 |
| 10,767,173 B2 | | 9/2020 | Mukoyama et al. | |
| 2005/0208489 A1 | | 9/2005 | Carroll et al. | |
| 2011/0002889 A1 | | 1/2011 | Barrangou et al. | |
| 2011/0104787 A1 | | 5/2011 | Church et al. | |
| 2011/0145940 A1 | | 6/2011 | Voytas et al. | |
| 2014/0294773 A1 | | 10/2014 | Brouns et al. | |
| 2014/0304853 A1 | | 10/2014 | Ainley et al. | |
| 2014/0335521 A1 | | 11/2014 | Nakamura et al. | |
| 2014/0356867 A1 | | 12/2014 | Peter et al. | |
| 2015/0031134 A1 | | 1/2015 | Zhang et al. | |
| 2015/0044772 A1 | | 2/2015 | Zhao | |
| 2015/0166980 A1 | | 6/2015 | Liu et al. | |
| 2015/0232882 A1 | | 8/2015 | Zhang et al. | |
| 2015/0315576 A1 | | 11/2015 | Caliando et al. | |
| 2016/0200779 A1 | | 7/2016 | Liu et al. | |
| 2017/0073670 A1 | | 3/2017 | Nishida et al. | |
| 2017/0121693 A1 | | 5/2017 | Liu et al. | |
| 2017/0321210 A1 | | 11/2017 | Nishida et al. | |
| 2019/0024098 A1 | | 1/2019 | Nishida et al. | |
| 2019/0085342 A1 | | 3/2019 | Nishida et al. | |
| 2019/0203198 A1 | | 7/2019 | Mukoyama et al. | |

(Continued)

FOREIGN PATENT DOCUMENTS

| | | | |
|---|---|---|---|
| CA | 2933625 | A1 | 6/2015 |
| CN | 102770539 | A | 11/2012 |

(Continued)

OTHER PUBLICATIONS

Komor et al. Programmable editing of a target base in genomic DNA without double-stranded DNA cleavage. Nature, vol. 533, pp. 420-424, including pp. 1/2-2/2 of Methods, and pp. 1/10-10/10 of Extended Data, published Apr. 20, 2016. (Year: 2016).*
Makarova et al. An updated evolutionary classification of CRISPR-Cas systems. Nature Reviews. Microbiology. vol. 13, No. 11, pp. 722-736, Epub Sep. 28, 2015. (Year: 2015).*
Nishida et al. Targeted nucleotide editing using hybrid prokaryotic and vertebrate adaptive immune systems. Science, vol. 353, No. 6305, aaf8729, Epub Aug. 4, 2016, printed as pp. 1-8, including pp. 1/35-35/35 of Supplementary Materials. (Year: 2016).*
Ramakrishna et al. Gene disruption by cell-penetrating peptide-mediated delivery of Cas9 protein and guide RNA. Genome Research, vol. 24, pp. 1020-1027, Apr. 2014, including pp. 1-11 of Supplemental Information. (Year: 2014).*

(Continued)

*Primary Examiner* — Nancy J Leith
(74) *Attorney, Agent, or Firm* — Leydig, Voit & Mayer, Ltd.

(57) ABSTRACT

The present invention provides a method of modifying a targeted site of a double-stranded DNA, comprising a step of introducing a complex wherein a nucleic acid sequence-recognizing module that specifically binds to a target nucleotide sequence in a double-stranded DNA and PmCDA1 are bonded, into a cell containing the double-stranded DNA, and culturing the cell at a low temperature at least temporarily to convert the targeted site, i.e., the target nucleotide sequence and nucleotides in the vicinity thereof, to other nucleotides, or delete the targeted site, or insert nucleotide into the site.

12 Claims, 2 Drawing Sheets

Specification includes a Sequence Listing.

(56) References Cited

U.S. PATENT DOCUMENTS

| | | | | |
|---|---|---|---|---|
| 2020/0208138 | A1 | 7/2020 | Nishida et al. | |
| 2020/0248174 | A1 * | 8/2020 | Nishida | C12N 9/22 |

FOREIGN PATENT DOCUMENTS

| | | | | |
|---|---|---|---|---|
| CN | 104854241 | A | 8/2015 | |
| CN | 105934516 | A | 9/2016 | |
| EP | 3115457 | A1 | 1/2017 | |
| EP | 3241902 | B1 | 2/2018 | |
| JP | 2010-519929 | A | 6/2010 | |
| JP | 4968498 | B2 | 7/2012 | |
| JP | 2013-513389 | A | 4/2013 | |
| JP | 2013-128413 | A | 7/2013 | |
| JP | 2015-503535 | A | 2/2015 | |
| WO | WO 2010/132092 | A2 | 11/2010 | |
| WO | WO 2011/072246 | A2 | 6/2011 | |
| WO | WO 2013/058404 | A1 | 4/2013 | |
| WO | WO 2013/098244 | A1 | 7/2013 | |
| WO | WO 2013/140250 | A1 | 9/2013 | |
| WO | WO 2013/176772 | A1 | 11/2013 | |
| WO | WO-2014018423 | A2 * | 1/2014 | C12N 15/102 |
| WO | WO 2014/020608 | A1 | 2/2014 | |
| WO | WO 2014/071235 | A1 | 5/2014 | |
| WO | WO 2014/093595 | A1 | 6/2014 | |
| WO | WO 2014/093712 | A1 | 6/2014 | |
| WO | WO 2014/186686 | A2 | 11/2014 | |
| WO | WO 2015/035136 | A2 | 3/2015 | |
| WO | WO 2015/089406 | A1 | 6/2015 | |
| WO | WO 2015/133554 | A1 | 9/2015 | |
| WO | WO 2016/072399 | A1 | 5/2016 | |
| WO | WO-2016069283 | A1 * | 5/2016 | A61P 35/00 |
| WO | WO 2017/070632 | A2 | 4/2017 | |
| WO | WO 2017/090761 | A1 | 6/2017 | |

OTHER PUBLICATIONS

Kim et al. Highly efficient RNA-guided genome editing in human cells via delivery of purified Cas9 ribonucleoproteins. Genome Research, vol. 24, pp. 1012-1019, Apr. 2, 2014, including pp. 1-7 of supplemental information. (Year: 2014).*

Remy et al. Efficient gene targeting by homology-directed repair in rat zygotes using TALE nucleases. Genome Research. vol. 24, pp. 1371-1383, Jul. 2, 2014, including Supplemental Figures 1 and 2, printed as pp. 1/2-2/2, and Supplemental Material, printed as pp. 1/11-11/11. (Year: 2014).*

Lada, A. G. (2014). Mechanisms of regulation of AID/APOBEC deaminases activity and protection of the genome from promiscuous deamination (Order No. 3581548). Available from ProQuest Dissertations & Theses Global. (1586125454). (Year: 2017).*

Al-Fageeh et al. The cold-shock response in cultured mammalian cells: Harnessing the response for the improvement of recombinant protein production. Biotechnology and Bioengineering. vol. 93, No. 5, pp. 829-835, Apr. 2006, published online Dec. 2, 2005. (Year: 2005).*

Mateus et al. Lampreys of the Iberian Peninsula: distribution, population status and conservation. Endangered Species Research, vol. 16, pp. 183-198, Feb. 29, 2012. (Year: 2012).*

Rieder et al. Cold-shock and the mammalian cell cycle. Cell Cycle, vol. 1, No. 3, pp. 169-175 2002. (Year: 2002).*

Nelson et al. Survival of synchronized mammalian cells following exposure to cold. Experimental Cell Research, vol. 70, pp. 417-422, 1972. (Year: 1972).*

Rogozin et al. Evolution and diversification of lamprey antigen receptors: evidence for involvement of an AID-APOBEC family of cytosine deaminase. Nature Immunology, vol. 8, No. 6, pp. 647-656, and pp. 1/88-88/88 of Supplementary Materials, Apr. 29, 2007. (Year: 2007).*

Chen et al. Engineered viruses as genome editing devices. Molecular Therapy, vol. 24, No. 3, pp. 447-457, Mar. 2016, published online Sep. 4, 2015. (Year: 2015).*

Wolf et al., "tadA, an essential tRNA-specific adenosine deaminase from *Escherichia coli*," *EMBO J.*, 21(14): 3841-3851 (2002).

Arazoe et al., "Targeted Nucleotide Editing Technologies for Microbial Metabolic Engineering," *Biotechnol. J.*, 13(9): e1700596 (2018).

Mitsunobu et al., "Beyond Native Cas9: Manipulating Genomic Information and Function," *Trends Biotechnol.*, 35(10): 983-996 (2017).

European Patent Office, Communication Pursuant to Article 94(3) EPC in European Patent Application No. 19196085.5 (Jan. 12, 2021).

Canadian Intellectual Property Offce, Examination Report in Canadian Patent Application No. 2,947,941 (Mar. 18, 2019).

European Patent Office, Communication Pursuant to Article 94(3) EPC in European Patent Application No. 15758734.6 (Apr. 4, 2019).

China National Intellectual Property Administration, Office Action and Search Report in Chinese Patent Application No. 201680079887.5 (May 18, 2021).

Chinese Patent Office, Second Office Action in Chinese Patent Application No. 201580023875.6 (May 7, 2019).

Jinek et al., "Structures of Cas9 Endonucleases Reveal RNA-Mediated Conformational Activation," *Science*, 343(6176): 1247997 and Supplementary Materials (2014).

Sinkunas et al., "Cas3 is a single-stranded DNA nuclease and ATP-dependent helicase in the CRISPR/Cas immune system," *EMBO J.*, 30: 1335-1342 (2011).

Finney-Manchester et al., "Harnessing mutagenic homologous recombination for targeted mutagenesis in vivo by TaGTEAM," *Nucleic Acids Res.*, 41(9): e99 (2013).

O'Connell et al., "Programmable RNA recognition and cleavage by CRISPR/Cas9," *Nature*, 516(7530): 263-266 (2014).

Szyf et al., "Maternal care, the epigenome and phenotypic differences in behavior," *Reprod. Toxicol.*, 24(1): 9-19 (2007).

Xu et al., "Efficient Genome Editing in *Clostridium cellulolyticum* via CRISPR-Cas9 Nickase," *Appl. Environ. Microbiol.*, 81(13): 4423-4431 and Supplementary Data (2015).

Zeng et al., "Highly efficient editing of the actinorhodin polyketide chain length factor gene in *Streptomyces coelicolor* M145 using CRISPR/Cas9-CodA(sm) combined system," *Appl. Microbiol. Biotechnol.*, 99(24): 10575-10585 (2015).

Japanese Patent Office, International Search Report in International Patent Application No. PCT/JP2016/076448 (Dec. 6, 2016).

Japanese Patent Office, International Search Report in International Patent Application No. PCT/JP2016/076711 (Nov. 29, 2016).

Bogdanove et al., "TAL Effectors: Customizable Proteins for DNA Targeting," *Science*, 333(6051): 1843-1846 (2011).

Cermak et al., "Efficient design and assembly of custom TALEN and other TAL effector-based constructs for DNA targeting," *Nucleic Acids Research*, 39(12): e82 (2011).

Cho et al., "Targeted genome engineering in human cells with the Cas9 RNA-guided endonuclease," *Nat. Biotechnol.*, 31(3): 230-232 (2013).

Cong et al., "Multiplex Genome Engineering Using CRISPR/Cas Systems," *Science*, 339(6121): 819-823 (2013).

Conticello et al., "Evolution of the AID/APOBEC Family of Polynucleotide (Deoxy)cytidine Deaminases," *Mol. Biol. Evol.*, 22(2): 367-377 (2005).

Dicarlo et al., "Genome engineering in *Saccharomyces cerevisiae* using CRISPR-Cas systems," *Nucleic Acids Res.*, 41(7): 4336-4343 (2013).

Esvelt et al., "Genome-scale engineering for systems and synthetic biology," *Molecular Systems Biology*, 9: 641 (2013).

Fang et al., "New Method of Genome Editing Derived From CRISPR/Cas9," *Prog. Biochem. Biophys.* 40(8): 691-702 (2013).

Gilbert et al., "CRISPR-Mediated Modular RNA-Guided Regulation of Transcription in Eukaryotes," *Cell*, 154(2): 442-451 (2013).

Horvath et al., "CRISPR/Cas, the Immune System of Bacteria and Archaea," *Science*, 327: 167-170 (2010).

Jiang et al., "RNA-guided editing of bacterial genomes using CRISPR-Cas systems," *Nat. Biotechnol.*, 31(3): 233-239 and online methods (2013).

(56) References Cited

OTHER PUBLICATIONS

Jinek et al., "A Programmable Dual-RNA-Guided DNA Endonuclease in Adaptive Bacterial Immunity," *Science*, 337(6096): 816-821 (2012).
Jinek et al., "RNA-programmed genome editing in human cells," *eLIFE*, 2: e00471 (2013).
Kim et al., "Genome-wide target specificities of CRISPR RNA-guided programmable deaminases," *Nat. Biotechnol.*, 35(5): 475-480 (2017).
Kitamura et al., "Uracil DNA Glycosylase Counteracts APOBEC3G-Induced Hypermutation of Hepatitis B Viral Genomes: Excision Repair of Covalently Closed Circular DNA," *PLoS Pathog.*, 9(5): e1003361 (2013).
Komor et al., "Programmable editing of a target base in genomic DNA without double-stranded DNA cleavage," *Nature*, 533(7603): 420-424 (2016).
Krokan et al., "Base Excision Repair," *Cold Spring Harb. Perspect. Biol.*, 5(4): a012583 (2013).
Lada et al., "AID/APOBEC cytosine deaminase induces genome-wide kataegis," *Biol. Direct*, 7: 47 (2012).
Lada et al., "Genome-Wide Mutation Avalanches Induced in Diploid Yeast Cells by a Base Analog or an APOBEC Deaminase," *PLoS Genet.*, 9(9): e1003736 (2013).
Makarova et al., "Evolution and classification of the CRISPR-Cas systems," *Nat. Rev. Microbiol.*, 9(6): 467-477 (2011).
Mali et al., "CAS9 transcriptional activators for target specificity screening and paired nickases for cooperative genome engineering," *Nat. Biotechnol.*, 31(9): 833-838 and online methods (2013).
Mali et al., "Cas9 as a versatile tool for engineering biology," *Nat. Methods*, 10(10): 957-963 (2013).
Mali et al., "RNA-Guided Human Genome Engineering via Cas9," *Science*: 339(6121): 823-826 (2013).
Mussolino et al., "TALE nucleases: tailored genome engineering made easy," *Current Opinion in Biotechnology*, 23(5): 644-650 (2012).
Nishida et al., "Targeted nucleotide editing using hybrid prokaryotic and vertebrate adaptive immune systems," *Science*, 353(6305): aaf8729 (2016).
Osakabe et al., "Genome Editing with Engineered Nucleases in Plants," *Plant Cell Physiol.*, 56(3): 389-400 (2015).
Perez-Pinera et al., "RNA-guided gene activation by CRISPR-Cas9-based transcription factors," *Nat. Methods*, 10(10): 973-976 (2013).
Pingoud et al., "Type II restrictions endonucleases—a historical perspective and more," *Nucleic Acids Res.*, 42(12): 7489-7527 (2014).
Plosky, "CRISPR-Mediated Base Editing without DNA Double-Strand Breaks," *Mol. Cell.*, 62(4): 477-478 (2016).
Ran et al., "Double Nicking by RNA-Guided CRISPR Cas9 for Enhanced Genome Editing Specificity," *Cell*, 154(6): 1380-1389 (2013).
Ran et al., "Genome engineering using the CRISPR-Cas9 system," *Nat. Protoc.*, 8(11): 2281-2308 (2013).
Rittié et al., "Enzymes used in molecular biology: a useful guide," *J. Cell. Commun. Signal.*, 2(1-2): 25-45 (2008).
Rogozin et al., "Evolution and diversification of lamprey antigen receptors: evidence for involvement of an AID-APOBEC family cytosine deaminase," *Nat. Immunol.*, 8(6): 647-656 and Supplementary Table 1 (2007).
Shalem et al., "Genome-Scale CRISPR-Cas9 Knockout Screening in Human Cells," *Science*, 343(6166): 84-87 and Supplementary Materials (2014).
Shimatani et al., "Targeted base editing in rice and tomato using a CRISPR-Cas9 cytidine deaminase fusion," *Nat. Biotechnol.*, 35(5): 441-443, Online Methods, and Corrigendum (2017).
Shmakov et al., "Discovery and Functional Characterization of Diverse Class 2 CRISPR-Cas Systems," *Mol Cell*, 60(3): 385-397 (2015).
Zetsche et al., "Cpf1 Is a Single RNA-Guided Endonuclease of a Class 2 CRISPR-Cas System," *Cell*, 163(3): 759-771 (2015).
Canadian Intellectual Property Office, Official Action and Examination Search Report in Canadian Patent Application No. 2,947,941 (Dec. 15, 2017).
Canadian Intellectual Property Office, Examination Report in Canadian Patent Application No. 2,947,941 (Jun. 22, 2018).
Chinese Patent Office, First Office Action in Chinese Patent Application No. 201580023875.6 (Sep. 3, 2018).
European Patent Office, Communication Pursuant to Article 94(3) EPC in European Patent Application No. 15758734.6 (May 4, 2018).
Japanese Patent Office, International Preliminary Report on Patentability in International Patent Application No. PCT/JP2015/056436 (May 10, 2016).
Japanese Patent Office, International Search Report in International Patent Application No. PCT/JP2015/056436 (Jun. 9, 2015).
Japanese Patent Office, International Search Report in International Patent Application No. PCT/JP2016/085075 (Feb. 21, 2017).
Japanese Patent Office, International Search Report in International Patent Application No. PCT/JP2017/016105 (Jul. 25, 2017).
Japanese Patent Office, Official Action in Japanese Patent Application No. 2017-164703 (May 16, 2018).
U.S. Appl. No. 15/124,021, filed Nov. 9, 2016, Pending.
U.S. Appl. No. 15/757,243, filed Mar. 2, 2018, Pending.
U.S. Appl. No. 15/757,646, filed Mar. 5, 2018, Pending.
U.S. Appl. No. 15/779,120, filed May 25, 2018, Pending.
Intellectual Property Office of Singapore, Written Opinion in Singaporean Patent Application No. 11201809242V (Feb. 25, 2021).
Intellectual Property Office of Singapore, Invitation to Respond to Written Opinion in Singaporean Patent Application No. 11201809242V (Feb. 26, 2021).
Japanese Patent Office, Official Action in Japanese Patent Application No. 2018-513234 (Feb. 24, 2021).
Lada et al., "Mutator Effects and Mutation Signatures of Editing Deaminases Produced in Bacteria and Yeast," *Biochemistry (Moscow)*, 76(1): 131-146 (2011).
Bortesi et al., "The CRISPR/Cas9 system for plant genome editing and beyond," *Biotechnol. Adv.*, 33(1): 41-52 (2015).
U.S. Appl. No. 16/791,968, filed Feb. 14, 2020, Pending.
U.S. Appl. No. 16/838,960, filed Apr. 2, 2020, Pending.
Char et al., "Heritable site-specific mutagenesis using TALENs in maize," *Plant Biotechnol. J.*, 13(7): 1002-1010 (2015).
Kuscu et al., "CRISPR-Cas9-AID base editor is a powerful gain-of-function screening tool," *Nat. Methods*, 13(12): 983-984 (2016).
Ma et al., "Targeted AID-mediated mutagenesis (TAM) enables efficient genomic diversification in mammalian cells," *Nat. Methods*, 13(12): 1029-1035 and Online Methods (2016).
European Patent Office, Extended European Search Report in European Patent Application No. 17786061.6 (Sep. 4, 2019).
China National Intellectual Property Administration, First Office Action and Search Report in Chinese Patent Application No. 201680065297.7 (Jan. 6, 2021).
Freitas et al., "Mechanisms and Signals for the Nuclear Import of Proteins," *Curr. Genomics*, 10(8): 550-557 (2009).
Harris et al., "RNA Editing Enzyme APOBEC1 and Some of Its Homologs Can Act as DNA Mutators," *Mol. Cell*, 10(5): 1247-1253 (2002).
European Patent Office, Communication Pursuant to Article 94(3) EPC in European Patent Application No. 16844517.9 (Apr. 14, 2021).
European Patent Office, Summons to Attend Oral Proceedings Pursuant to Rule 115(1) EPC in European Patent Application No. 16868704.4 (May 27, 2021).
European Patent Office, Communication Pursuant to Article 94(3) EPC in European Patent Application No. 19196085.5 (May 31, 2022).
Fonfara et al., "Phylogeny of Cas 9 Determines Functional Exchangeability of Dual-RNA and Cas9 among Orthologous Type II CRISPR-Cas Systems," *Nucleic Acids Res.*, 42(4): 2577-2590 (2014).
Fu et al., "Target-Dependent Nickase Activities of CRISPR-Cas Nucleases Cpf1 and Cas9," *Nat. Microbiol.*, 4(5): 888-897 (2019).
Genbank Database, "Multiple Alignment of *S. pyogenes* Cas9 Amino Acid Sequences," *GenBank National Center for Biotechnology Information* (2022).

(56) References Cited

OTHER PUBLICATIONS

Hsu et al., "Development and Applications of CRISPR-Cas9 for Genome Engineering," *Cell*, 157(6): 1262-1278 (2014).
Koonin et al, "CRISPR-CAS—Evolution of an RNA-based Adaptive Immunity System in Prokaryotes," *RNA Biology*, 10(5): 679-686 (2013).
Makarova et al., "Evolutionary Classification of CRISPR-Cas Systems: A Burst of Class 2 and Derived Variants," *Nat. Rev. Microbiol.*, 18(2): 67-83 (2020).
Marakova et al., "Classification and Nomenclature of CRISPR-Cas Systems: Where from Here?," *CRISPR J.*, 1(5): 325-336 (2018).
Stafforst et al., "An RNA-Deaminase Conjugate Selectively Repairs Point Mutations," *Angew. Chem. Int. Ed.*, 51(44): 11166-11169 (2012).
Yan et al., "Functionally Diverse Type V CRISPR-Cas Systems," *Science.*, 363(6422): 88-91 (2019).
China National Intellectual Property Administration, Decision of Final Rejection in Chinese Patent Application No. 201680065298.1 (Apr. 25, 2022).
European Patent Office, Brief Communication in European Patent Application No. 15758734.6 (Mar. 4, 2022).
Canadian Intellectual Property Office, Office Action in Canadian Patent Application No. 2,998,087 (Aug. 4, 2022).
Japan Patent Office, Decision of Refusal in Japanese Patent Application No. 2020-073425 (Jul. 12, 2022).
Farzadfard et al., "Turnable and Multifunctional Eukaryotic Transcription Factors Based on CRISPR/Cas," *ACS Synth. Biol.*, 2(10): 604-613 (2013).
Ma et al., "Multicolor CRISPR labeling of chromosomal loci in human cells," *Proc. Natl. Acad. Sci. U.S.A.*, 112(10): 3002-3007 and Supporting Information (2015).
Brazilian National Institute of Industrial Property, Written Opinion in Brazilian Patent Application No. BR112018071376-7 (Sep. 16, 2022).
China National Intellectual Property Administration, Office Action in Chinese Patent Application No. 201780038364.0 (Sep. 5, 2022).
China National Intellectual Property Administration, Office Action in Chinese Patent Application No. 202010159183.7 (Feb. 20, 2023).
Kaufmann et al., "Influence of Low Temperature on Productivity, Proteome and Protein Phosphorylation of CHO Cells," *Biotechnol. Bioeng.*, 63(5): 573-582 (1999).
Kumar et al., "Differential Protein Expression Following Low Temperature Culture of Suspension CHO-K1 Cells," *BMC Biotechnol.*, 8: 42 (2008).
Mali et al., "RNA-Guided Human Genome Engineering via Cas9," *Science.*, 339(6121): 823-826 and Supplementary Materials (2013), pp. 1-8 and 1/38-38/38 of Supplementary Materials.
Moore et al., "Effects of Temperature Shift on Cell Cycle, Apoptosis and Nucleotide Pools in CHO Cell Batch Cultues [sic—Cultures]," *Cytotechnology*. 23(1-3): 47-54 (1997).
Xiang et al., "Temperature Effect on CRISPR-Cas9 Mediated Genome Editing," *J. Genet. Genomics*, 44(4): 199-205 (2017).
China National Intellectual Property Administration, Third Office Action in Chinese Patent Application No. 201780038364.0 (Jan. 20, 2023).
European Patent Office, Communication Pursuant to Article 94(3) EPC in European Patent Application No. 19196085.5 (Jun. 21, 2023).
China National Intellectual Property Administration, Office Action in Chinese Patent Application No. 202010158495.6 (Apr. 20, 2024).

* cited by examiner

METHOD FOR INCREASING MUTATION INTRODUCTION EFFICIENCY IN GENOME SEQUENCE MODIFICATION TECHNIQUE, AND MOLECULAR COMPLEX TO BE USED THEREFOR

CROSS-REFERENCE TO RELATED APPLICATIONS

This patent application is the U.S. national phase of International Patent Application No. PCT/JP2017/016105, filed Apr. 21, 2017, which claims the benefit of Japanese Patent Application No. 2016-085631, filed on Apr. 21, 2016, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing identified as follows: 51,991 bytes ASCII (Text) file named "740935ReplacementSequenceListing.txt," created Jan. 27, 2022.

TECHNICAL FIELD

The present invention relates to a method for improving mutation introduction efficiency of a genome sequence modification technique that enables modification of a nucleic acid base in a particular region of a genome without cleaving double-stranded DNA, i.e., with no cleavage or single strand cleavage, or inserting a foreign DNA fragment, and a complex of a nucleic acid sequence-recognizing module, a nucleic acid base converting enzyme and a base excision repair inhibitor to be used therefor.

BACKGROUND ART

In recent years, genome editing is attracting attention as a technique for modifying the object gene and genome region in various species. Conventionally, as a method of genome editing, a method utilizing an artificial nuclease comprising a molecule having a sequence-independent DNA cleavage ability and a molecule having a sequence recognition ability in combination has been proposed (non-patent document 1).

For example, a method of performing recombination at a target gene locus in DNA in a plant cell or insect cell as a host, by using a zinc finger nuclease (ZFN) wherein a zinc finger DNA binding domain and a non-specific DNA cleavage domain are linked (patent document 1), a method of cleaving or modifying a target gene in a particular nucleotide sequence or a site adjacent thereto by using TALEN wherein a transcription activator-like (TAL) effector which is a DNA binding module that the plant pathogenic bacteria *Xanthomonas* has, and a DNA endonuclease are linked (patent document 2), a method utilizing CRISPR-Cas9 system wherein DNA sequence CRISPR (Clustered Regularly interspaced short palindromic repeats) that functions in an acquired immune system possessed by eubacterium and archaebacterium, and nuclease Cas (CRISPR-associated) protein family having an important function along with CRISPR are combined (patent document 3) and the like have been reported. Furthermore, a method of cleaving a target gene in the vicinity of a particular sequence, by using artificial nuclease wherein a PPR protein constituted to recognize a particular nucleotide sequence by a continuation of PPR motifs each consisting of 35 amino acids and recognizing one nucleic acid base, and nuclease are linked (patent document 4) has also been reported.

These genome editing techniques basically presuppose double-stranded DNA breaks (DSB). However, since they include unexpected genome modifications, side effects such as strong cytotoxicity, chromosomal rearrangement and the like occur, and they have common problems of impaired reliability in gene therapy, extremely small number of surviving cells by nucleotide modification, and difficulty in genetic modification itself in primate ovum and unicellular microorganisms.

On the other hand, as a method for performing nucleotide modification without accompanying DSB, the present inventors reported that, in the CRISPR-Cas system wherein at least one DNA cleavage ability of Cas is inactivated, a genome sequence was successfully modified without accompanying DSB and by nucleobase conversion in a region containing a specific DNA sequence. In the system, they used deaminase that catalyzes a deamination reaction, which was linked to a molecule having a DNA sequence recognition ability (patent document 5). According to this genome editing technique, since the technique does not involve insertion of foreign DNA or cleavage of DNA double strand, it is superior in safety, and the range of mutation introduction can theoretically be set widely from a single base pinpoint to several hundred bases. However, there was a problem that efficiency of mutation introduction is low as compared to genome editing technique using Cas9 having normal DNA cleaving ability.

In genome editing technique, moreover, a method for enhancing the efficiency of mutation introduction by shifting the culture temperature of the cell to a low temperature has not been reported. In addition, there is no report teaching that the activity of Petromyzon marinus-derived PmCDA1 (Petromyzon marinus cytosine deaminase 1), which is one kind of deaminase, is enhanced when the temperature is lower than about 37° C. which is the optimal temperature of general enzymes.

DOCUMENT LIST

Patent Documents patent document 1: JP-B-4968498
patent document 2: National Publication of International Patent Application No. 2013-513389
patent document 3: National Publication of International Patent Application No. 2010-519929
patent document 4: JP-A-2013-128413
patent document 5: WO 2015/133554

Non-Patent Document non-patent document 1: Kelvin M Esvelt, Harris H Wang (2013) Genome-scale engineering for systems and synthetic biology, Molecular Systems Biology 9: 641

SUMMARY OF THE INVENTION

Problems to be Solved by the Invention

An object of the present invention is to provide a genome editing method for improving mutation introduction efficiency by modifying nucleic acid bases of a particular sequence of a gene by not cleaving double-stranded DNA or cleaving single strand, and a complex therefor of a nucleic acid sequence-recognizing module, a nucleic acid base converting enzyme, and a base excision repair inhibitor.

Means of Solving the Problems

The present inventors searched for the development of a method for improving the mutation introduction efficiency in the genome editing technique using a nucleic acid base converting enzyme. In the development of a method for improving mutation introduction efficiency, in general, the focus is placed on a method for increasing the nucleic acid base converting ability by artificially mutating a nucleic acid base converting enzyme or replacing same with other enzyme, or a method for increasing the nucleic acid recognizing ability of a nucleic acid sequence-recognizing module and the like. The present inventors changed these general ideas and assumed that, in the genome editing technique, one of the causes of the low mutation introduction efficiency might be that the mechanism of base excision repair by DNA glycosylase or the like works at the site where the base was converted by the nucleic acid base converting enzyme and the introduced mismatch is repaired. They then had an idea that the mutation introduction efficiency might be increased by inhibiting proteins acting on the base excision repair mechanisms. Thus, the present inventors coexpressed a uracil DNA glycosylase inhibitor (Ugi) that inhibits repair of deaminated bases, and found that the mutation introduction efficiency was strikingly improved.

PmCDA1, which is one kind of nucleic acid base converting enzyme, is derived from Petromyzon marinus, a poikilothermic animal. Thus, they assumed that the optimal temperature for the enzyme activity of PmCDA1 might be lower than about 37° C., which is the optimal temperature for general enzymes, and had an idea that the enzyme activity might be enhanced by adjusting the culture temperature. In an attempt to enhance the enzyme activity of PmCDA1, therefore, they cultured the cells transfected with PmCDA1 temporarily at a low temperature and found that the mutation introduction efficiency was improved.

The present inventor have conducted further studies based on these findings and completed the present invention.

Therefore, the present invention is as described below.

[1] A method of modifying a targeted site of a double-stranded DNA, comprising a step of introducing a complex wherein a nucleic acid sequence-recognizing module that specifically binds to a target nucleotide sequence in a given double-stranded DNA and PmCDA1 are bonded, into a cell containing the double-stranded DNA, and culturing the cell at a low temperature at least temporarily to convert one or more nucleotides in the targeted site to other one or more nucleotides or delete one or more nucleotides, or insert one or more nucleotides into said targeted site, without cleaving at least one strand of said double-stranded DNA in the targeted site, P1 wherein the nucleic acid sequence-recognizing module is a CRISPR-Cas system wherein at least one DNA cleavage ability of Cas is inactivated.

[2] The method of [1], wherein the aforementioned Cas is deficient in two DNA cleavage abilities.

[3] The method of [1] or [2], wherein the aforementioned cell is a mammalian cell.

[4] The method of [3], wherein the low temperature is 20° C. to 35° C.

[5] The method of [3], wherein the low temperature is 25° C.

[6] The method of any of [1] to [5], wherein the double-stranded DNA is contacted with the complex by introducing a nucleic acid encoding the complex into a cell having the double-stranded DNA.

[7] A method of modifying a targeted site of a double-stranded DNA, comprising a step of contacting a complex wherein a nucleic acid sequence-recognizing module that specifically binds to a target nucleotide sequence in a given double-stranded DNA, a nucleic acid base converting enzyme and a base excision repair inhibitor are bonded, with said double-stranded DNA to convert one or more nucleotides in the targeted site to other one or more nucleotides or delete one or more nucleotides, or insert one or more nucleotides into said targeted site, without cleaving at least one strand of said double-stranded DNA in the targeted site, wherein the nucleic acid sequence-recognizing module is a CRISPR-Cas system wherein at least one DNA cleavage ability of Cas is inactivated.

[8] The method of [7], wherein the aforementioned Cas is deficient in two DNA cleavage abilities.

[9] The method of [7] or [8], wherein the aforementioned nucleic acid base converting enzyme is cytidine deaminase.

[10] The method of [9], wherein the aforementioned cytidine deaminase is PmCDA1.

[11] The method of [9] or [10], wherein the base excision repair inhibitor is a uracil DNA glycosylase inhibitor.

[12] The method of any of [7] to [11], wherein the double-stranded DNA is contacted with the complex by introducing a nucleic acid encoding the complex into a cell having the double-stranded DNA.

[13] The method of [12], wherein the aforementioned cell is a mammalian cell.

[14] A nucleic acid-modifying enzyme complex wherein a nucleic acid sequence-recognizing module that specifically binds to a target nucleotide sequence in a given double-stranded DNA, a nucleic acid base converting enzyme and a base excision repair inhibitor are bonded, which complex converts one or more nucleotides in the targeted site to other one or more nucleotides or deletes one or more nucleotides, or inserts one or more nucleotides into said targeted site, without cleaving at least one strand of said double-stranded DNA in the targeted site, wherein the nucleic acid sequence-recognizing module is a CRISPR-Cas system wherein at least one DNA cleavage ability of Cas is inactivated.

[15] A nucleic acid encoding the nucleic acid-modifying enzyme complex of [14].

Effect of the Invention

According to the genome editing technique of the present invention, the mutation introduction efficiency is strikingly improved as compared to conventional genome editing techniques using nucleic acid base converting enzymes.

DESCRIPTION OF EMBODIMENTS

Figure 1:
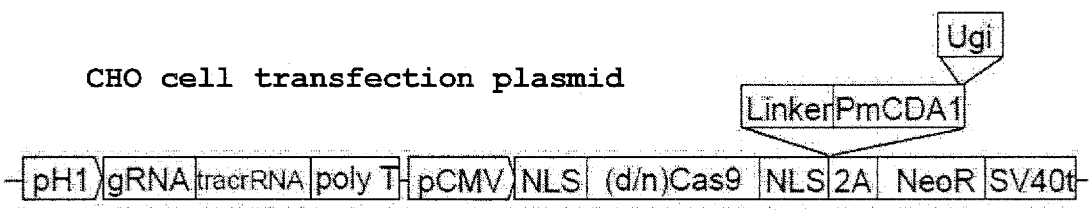
FIG. 1 is a schematic showing of the genome editing plasmid used in the Examples.

The present invention provides a method of improving mutation introduction efficiency in the genome editing technique including modifying a targeted site of a double stranded DNA by converting the target nucleotide sequence and nucleotides in the vicinity thereof in the double stranded DNA to other nucleotides, without cleaving at least one chain of the double stranded DNA to be modified. The method characteristically contains a step of introducing a complex wherein a nucleic acid sequence-recognizing module that specifically binds to the target nucleotide sequence in the double-stranded DNA and PmCDA1 are bonded into a cell having the double-stranded DNA, and culturing the cell at a low temperature at least temporarily to convert the targeted site, i.e., the target nucleotide sequence and nucleotides in the vicinity thereof, to other nucleotides, or delete the targeted site, or insert nucleotide into the site.

In another embodiment, the method characteristically contains a step of contacting a complex wherein a nucleic acid sequence-recognizing module that specifically binds to the target nucleotide sequence in the double-stranded DNA, a nucleic acid base converting enzyme, and a base excision repair inhibitor are bonded with the double-stranded DNA to convert the targeted site, i.e., the target nucleotide sequence and nucleotides in the vicinity thereof, to other nucleotides, or delete the targeted site, or insert nucleotide into the site.

In still another embodiment, the method characteristically contains a step of introducing a complex wherein a nucleic acid sequence-recognizing module that specifically binds to the target nucleotide sequence in the double-stranded DNA, and a nucleic acid base converting enzyme are bonded, into a cell having the double-stranded DNA, and inhibiting base excision repair of the cell to convert the targeted site, i.e., the target nucleotide sequence and nucleotides in the vicinity thereof, to other nucleotides, or delete the targeted site, or insert nucleotide into the site.

In the present invention, the "modification" of a double-stranded DNA means that a nucleotide (e.g., dC) on a DNA strand is converted to other nucleotide (e.g., dT, dA or dG), or deleted, or a nucleotide or a nucleotide sequence is inserted between certain nucleotides on a DNA strand. While the double-stranded DNA to be modified is not particularly limited, it is preferably a genomic DNA. The "targeted site" of a double-stranded DNA means the whole or partial "target nucleotide sequence", which a nucleic acid sequence-recognizing module specifically recognizes and binds to, or the vicinity of the target nucleotide sequence (one or both of 5' upstream and 3' downstream), and the range thereof can be appropriately adjusted between 1 base and several hundred bases according to the object.

In the present invention, the "nucleic acid sequence-recognizing module" means a molecule or molecule complex having an ability to specifically recognize and bind to a particular nucleotide sequence (i.e., target nucleotide sequence) on a DNA strand. Binding of the nucleic acid sequence-recognizing module to a target nucleotide sequence enables a nucleic acid base converting enzyme and a base excision repair inhibitor linked to the module to specifically act on a targeted site of a double-stranded DNA.

In the present invention, the "nucleic acid base converting enzyme" means an enzyme capable of converting a target nucleotide to other nucleotide by catalyzing a reaction for converting a substituent on a purine or pyrimidine ring on a DNA base to other group or atom, without cleaving the DNA strand.

In the present invention, the "base excision repair" is one of the DNA repair mechanisms of living organisms, and means a mechanism for repairing damages of bases by cutting off damaged parts of the bases by enzymes and rejoining them. Excision of damaged bases is performed by DNA glycosylase, which is an enzyme that hydrolyzes the N-glycosidic bond of DNA. An abasic site (apurinic/apyrimidic (AP) site) resulting from the abasic reaction by the enzyme is treated by an enzyme at the downstream of the base excision repair (BER) pathway such as AP endonuclease, DNA polymerase, DNA ligase and the like. Examples of such gene or protein involved in the BER pathway include, but are not limited to, UNG (NM_003362), SMUG1 (NM_014311), MBD4 (NM_003925), TDG (NM_003211), OGG1 (NM_002542), MYH (NM_012222), NTHL1 (NM_002528), MPG (NM_002434), NEIL1 (NM_024608), NEIL2 (NM_145043), NEIL3 (NM_018248), APE1 (NM_001641), APE2 (NM_014481), LIG3 (NM_013975), XRCC1 (NM_006297), ADPRT (PARP1) (NM_0016718), ADPRTL2 (PARP2) (NM_005484) and the like (parentheses indicate refseq number in which the base sequence information of each gene (cDNA) is registered).

In the present invention, the "base excision repair inhibitor" means a protein that consequently inhibits BER by inhibiting any of the stages of the above-mentioned BER pathway, or inhibiting the expression itself of the molecule mobilized by the BER pathway. In the present invention, "to inhibit base excision repair" means to consequently inhibit BER by inhibiting any of the stages of the above-mentioned BER pathway, or inhibiting the expression itself of the molecule mobilized by the BER pathway.

In the present invention, the "nucleic acid-modifying enzyme complex" means a molecular complex comprising a complex comprising the above-mentioned nucleic acid sequence-recognizing module and nucleic acid base converting enzyme are connected, and having nucleic acid base converting enzyme activity and imparted with a particular nucleotide sequence recognition ability. A base excision repair inhibitor may be further linked to the complex. The "complex" here encompasses not only one constituted of multiple molecules, but also one having a nucleic acid sequence-recognizing module and a nucleic acid base converting enzyme in a single molecule, like a fusion protein. In addition, "encoding the complex" encompasses both of encoding each molecule constituting the complex and encoding a fusion protein containing the constituting molecule in a single molecule.

In the present invention, the "low temperature" means a temperature lower than the general culture temperature for cell proliferation in cell culture. For example, when the general culture temperature of the cell is 37° C., a temperature lower than 37° C. corresponds to the low temperature. On the other hand, the low temperature needs to be a temperature that does not damage cells since the cells are damaged when the culture temperature is too low. While the low temperature varies depending on the cell type, culture period and other culture conditions, for example, when the cell is a mammalian cell such as Chinese hamster ovary (CHO) cell and the like, it is typically 20° C. to 35° C., preferably 20° C. to 30° C., more preferably 20° C. to 25° C., further preferably 25° C.

In the present invention, "culturing at a low temperature at least temporarily" means culturing a cell under the above-mentioned "low temperature conditions" for at least a part of the whole culture period and encompasses culturing at a low temperature for the whole culture period. In addition, culturing cells intermittently at a low temperature in multiple times during the culture period is also encompassed in "culturing at a low temperature at least temporarily". While the timing and duration of the low temperature culture is not particularly limited, generally, low temperature culture is maintained for not less than one night after introduction of the complex of a nucleic acid sequence-recognizing module and PmCDA1 or a nucleic acid encoding same into the cell. The upper limit of the culture period is not particularly limited as long as it is the minimum period necessary for modification of the targeted site of the double-stranded DNA, and the cells may be cultured at a low temperature for the whole culture period. While the whole culture period varies depending on the cell type, culture period and other culture conditions, for example, when a mammalian cell such as CHO cell and the like is cultured at 25° C., it is typically about 10 days to 14 days. In a preferable one embodiment, a mammalian cell such as CHO cell and the like is cultured for not less than one night, preferably one night to 7 days (e.g., overnight) after introduction of the complex at 20° C. to 35° C., preferably 20° C. to 30° C., more preferably 20° C. to 25° C., further preferably 25° C.

The nucleic acid base converting enzyme to be used in the present invention is not particularly limited as long as it can catalyze the above-mentioned reaction, and examples thereof include deaminase belonging to the nucleic acid/nucleotide deaminase superfamily, which catalyzes a deamination reaction that converts an amino group to a carbonyl group. Preferable examples thereof include cytidine deaminase capable of converting cytosine or 5-methylcytosine to uracil or thymine, respectively, adenosine deaminase capable of converting adenine to hypoxanthine, guanosine deaminase capable of converting guanine to xanthine and the like. As cytidine deaminase, more preferred is activation-induced cytidine deaminase (hereinafter to be also referred to as AID) which is an enzyme that introduces a mutation into an immunoglobulin gene in the acquired immunity of vertebrate or the like.

While the derivation of nucleic acid base converting enzyme is not particularly limited, for example, PmCDA1 derived from Petromyzon marinus (Petromyzon marinus cytosine deaminase 1), or AID (Activation-induced cytidine deaminase; AICDA) derived from mammal (e.g., human, swine, bovine, horse, monkey etc.) can be used. For example, GenBank accession Nos. EF094822 and ABO15149 can be referred to for the base sequence and amino acid sequence of cDNA of PmCDA1, GenBank accession No. NM_020661 and NP_065712 can be referred to for the base sequence and amino acid sequence of cDNA of human AID. From the aspect of enzyme activity, PmCDA1 is preferable. As shown in the below-mentioned Examples, it was found that the risk of off-target mutation can be suppressed even when Ugi is used in combination in a particular embodiment using PmCDA1 as cytidine deaminase. Therefore, from the aspect of reduction of the risk of off-target mutation, PmCDA1 is preferable.

While the base excision repair inhibitor to be used in the present invention is not particularly limited as long as it consequently inhibits BER, from the aspect of efficiency, an inhibitor of DNA glycosylase located at the upstream of the BER pathway is preferable. Examples of the inhibitor of DNA glycosylase to be used in the present invention include, but are not limited to, a thymine DNA glycosylase inhibitor, an uracil DNA glycosylase inhibitor, an oxoguanine DNA glycosylase inhibitor, an alkylguanine DNA glycosylase inhibitor and the like. For example, when cytidine deaminase is used as a nucleic acid base converting enzyme, it is suitable to use a uracil DNA glycosylase inhibitor to inhibit repair of U:G or G:U mismatch of DNA generated by mutation.

Examples of such uracil DNA glycosylase inhibitor include, but are not limited to, a uracil DNA glycosylase inhibitor (Ugi) derived from *Bacillus subtilis* bacteriophage, PBS1, and a uracil DNA glycosylase inhibitor (Ugi) derived from *Bacillus subtilis* bacteriophage, PBS2 (Wang, Z., and Mosbaugh, D. W. (1988) J. Bacteriol. 170, 1082-1091). The above-mentioned inhibiter of the repair of DNA mismatch can be used in the present invention. Particularly, Ugi derived from PBS2 is also known to have an effect of making it difficult to cause mutation, cleavage and recombination other than T from C on DNA, and thus the use of Ugi derived from PBS2 is suitable.

As mentioned above, in the base excision repair (BER) mechanism, when a base is excised by DNA glycosylase, AP endonuclease puts a nick in the abasic site (AP site), and exonuclease completely excises the AP site. When the AP site is excised, DNA polymerase produces a new base by using the base of the opposing strand as a template, and DNA ligase finally seals the nick to complete the repair. Mutant AP endonuclease that has lost the enzyme activity but maintains the binding capacity to the AP site is known to competitively inhibit BER. Therefore, these mutation AP endonucleases can also be used as the base excision repair inhibitor in the present invention. While the derivation of the mutant AP endonuclease is not particularly limited, for example, AP endonucleases derived from *Escherichia coli*, yeast, mammal (e.g., human, mouse, swine, bovine, horse, monkey etc.) and the like can be used. For example, UniprotKB No. P27695 can be referred to for the amino acid sequence of human Apel. Examples of the mutant AP endonuclease that has lost the enzyme activity but maintains the binding capacity to the AP site include proteins having mutated activity site and mutated Mg (cofactor)-binding site. For example, E96Q, Y171A, Y171F, Y171H, D210N, D210A, N212A and the like can be mentioned for human Apel.

The base excision repair of the cell can be inhibited by introducing an inhibitor of the aforementioned BER or a nucleic acid encoding same or a low-molecular-weight compound inhibiting BER. Alternatively, BER of the cell can be inhibited by suppressing the expression of a gene involved in the BER pathway. Suppression of gene expression can be performed, for example, by introducing siRNA capable of specifically suppressing expression of a gene involved in BER pathway, an antisense nucleic acid or an expression vector capable of expressing polynucleotides of these into cells. Alternatively, gene expression can be suppressed by knockout of genes involved in BER pathway.

Therefore, as one embodiment of the present invention, a method for improving the mutation introduction efficiency comprising a step of introducing a complex wherein a nucleic acid sequence-recognizing module that specifically binds to the target nucleotide sequence in the double-stranded DNA and a nucleic acid base converting enzyme are bonded into a cell containing the double-stranded DNA and showing suppressed expression of a gene relating to the BER pathway to convert the targeted site, i.e., the target nucleotide sequence and nucleotides in the vicinity thereof, to other nucleotides, or delete the targeted site, or insert nucleotide into the site is provided.

siRNA is typically a double-stranded oligo RNA consisting of an RNA having a sequence complementary to a nucleotide sequence of mRNA or a partial sequence thereof (hereinafter target nucleotide sequence) of the target gene, and a complementary strand thereof. The nucleotide sequences of these RNAs can be appropriately designed according to the sequence information of the genes involved in the BER pathway. It is a single-stranded RNA in which a sequence complementary to the target nucleotide sequence (first sequence) and a sequence complementary thereto (second sequence) are linked via a hairpin loop portion, and an RNA (small hairpin RNA: shRNA) in which the first sequence forms a double-stranded structure with the second sequence by adopting a hairpin loop type structure is also one of the preferable embodiments of siRNA.

The antisense nucleic acid means a nucleic acid containing a nucleotide sequence capable of specifically hybridizing with the target mRNA under physiological conditions of cells expressing the target mRNA (mature mRNA or initial transcription product) and capable of inhibiting translation of polypeptide coded by the target mRNA while being hybridized. The kind of the antisense nucleic acid may be DNA or RNA, or DNA/RNA chimera. The nucleotide sequence of these nucleic acids can be appropriately designed according to the sequence information of a gene involved in the BER pathway.

Knockout of genes involved in the BER pathway means that all or a part of the genes involved in the BER pathway have been destroyed or recombined so as not to exhibit their original functions. The gene may be destroyed or mutated so that one allele on the genome will not function and plural alleles may be destroyed or mutated. Knockout can be performed by a known method. For example, a method of knocking out by introducing a DNA construct made to cause genetic recombination with the target gene into the cell, a method of knocking out by insertion, deletion, substitution introduction of bases by using TALEN, CRISPR-Cas9 system or the like can be mentioned.

A target nucleotide sequence in a double-stranded DNA to be recognized by the nucleic acid sequence-recognizing module in the nucleic acid-modifying enzyme complex of the present invention is not particularly limited as long as the module specifically binds to, and may be any sequence in the double-stranded DNA. The length of the target nucleotide sequence only needs to be sufficient for specific binding of the nucleic acid sequence-recognizing module. For example, when mutation is introduced into a particular site in the genomic DNA of a mammal, it is not less than 12 nucleotides, preferably not less than 15 nucleotides, more preferably not less than 17 nucleotides, according to the genome size thereof. While the upper limit of the length is not particularly limited, it is preferably not more than 25 nucleotides, more preferably not more than 22 nucleotides.

As the nucleic acid sequence-recognizing module in the nucleic acid-modifying enzyme complex of the present invention, CRISPR-Cas system wherein at least one DNA cleavage ability of Cas is inactivated (hereinafter to be also referred to as “CRISPR-mutant Cas” and also encompasses CRISPR-mutant Cpf1), zinc finger motif, TAL effector and PPR motif and the like, as well as a fragment containing a DNA binding domain of a protein that specifically binds to DNA, such as restriction enzyme, transcription factor, RNA polymerase and the like, and free of a DNA double strand cleavage ability and the like can be used, but the module is not limited thereto. Preferably, CRISPR-mutant Cas, zinc finger motif, TAL effector, PPR motif and the like can be mentioned.

As a genome editing technique using CRISPR, a case using CRISPR-Cpf1 has been reported besides CRISPR-Cas9 (Zetsche B., et al., Cell, 163:759-771 (2015)). Cpf1 has properties different from Cas9 in that it does not require tracrRNA, that the cleaved DNA is a cohesive end, that the PAM sequence is present on the 5'-side and is a T-rich sequence and the like. Cpf1 capable of genome editing in mammalian cells includes, but is not limited to, Cpf1 derived from *Acidaminococcus* sp. BV3L6, Cpf1 derived from Lachnospiraceae bacterium ND2006 and the like. Mutant Cpf1 lacking DNA cleavage ability includes a D917A mutant in which the 917th Asp residue of Cpf1 (FnCpf1) derived from *Francisella novicida* U112 is converted to an Ala residue, an E1006A mutant obtained by converting the 1006th Glu residue to an Ala residue, a D1255A mutant obtained by converting the 1255th Asp residue to an Ala residue and the like. The mutant is not limited to these mutants and any mutant Cpf1 lacking the DNA cleavage ability can be used in the present invention.

A zinc finger motif is constituted by linkage of 3-6 different Cys2His2 type zinc finger units (1 finger recognizes about 3 bases), and can recognize a target nucleotide sequence of 9-18 bases. A zinc finger motif can be produced by a known method such as Modular assembly method (Nat Biotechnol (2002) 20: 135-141), OPEN method (Mol Cell (2008) 31: 294-301), CoDA method (Nat Methods (2011) 8: 67-69), *Escherichia coli* one-hybrid method (Nat Biotechnol (2008) 26:695-701) and the like. The above-mentioned patent document 1 can be referred to as for the detail of the zinc finger motif production.

A TAL effector has a module repeat structure with about 34 amino acids as a unit, and the 12th and 13th amino acid residues (called RVD) of one module determine the binding stability and base specificity. Since each module is highly independent, TAL effector specific to a target nucleotide sequence can be produced by simply connecting the module. For TAL effector, a production method utilizing an open resource (REAL method (Curr Protoc Mol Biol (2012) Chapter 12: Unit 12.15), FLASH method (Nat Biotechnol (2012) 30: 460-465), and Golden Gate method (Nucleic Acids Res (2011) 39: e82) etc.) have been established, and a TAL effector for a target nucleotide sequence can be designed comparatively conveniently. The above-mentioned patent document 2 can be referred to as for the detail of the production of TAL effector.

PPR motif is constituted such that a particular nucleotide sequence is recognized by a continuation of PPR motifs each consisting of 35 amino acids and recognizing one nucleic acid base, and recognizes a target base only by 1, 4 and ii(-2) amino acids of each motif. Motif constituent has no dependency, and is free of interference of motifs on both sides. Therefore, like TAL effector, a PPR protein specific to the target nucleotide sequence can be produced by simply connecting PPR motifs. The above-mentioned patent document 4 can be referred to as for the detail of the production of PPR motif.

When a fragment of restriction enzyme, transcription factor, RNA polymerase and the like is used, since the DNA binding domains of these proteins are well known, a fragment containing the domain and free of a DNA double strand cleavage ability can be easily designed and constructed.

Any of the above-mentioned nucleic acid sequence-recognizing module can be provided as a fusion protein with the above-mentioned nucleic acid base converting enzyme and/or base excision repair inhibitor, or a protein binding domain such as SH3 domain, PDZ domain, GK domain, GB domain and the like and a binding partner thereof may be fused with a nucleic acid sequence-recognizing module and a nucleic acid base converting enzyme and/or base excision repair inhibitor, respectively, and provided as a protein complex via an interaction of the domain and a binding partner thereof. Alternatively, a nucleic acid sequence-recognizing module and a nucleic acid base converting enzyme and/or base excision repair inhibitor may be each fused with intein, and they can be linked by ligation after protein synthesis.

The nucleic acid-modifying enzyme complex of the present invention may be contacted with a double-stranded DNA by introducing the complex or a nucleic acid encoding the complex into a cell having the object double-stranded DNA (e.g., genomic DNA). In consideration of the introduction and expression efficiency, it is desirable to introduce the complex in the form of a nucleic acid encoding same rather than the nucleic acid modifying enzyme complex itself, and express the complex in the cell.

Therefore, the nucleic acid sequence-recognizing module, the nucleic acid base converting enzyme and the base excision repair inhibitor are preferably prepared as a nucleic acid encoding a fusion protein thereof, or in a form capable of forming a complex in a host cell after translation into a protein by utilizing a binding domain, intein and the like, or as a nucleic acid encoding each of them. The nucleic acid here may be a DNA or an RNA. When it is a DNA, it is preferably a double-stranded DNA, and provided in the form of an expression vector disposed under regulation of a functional promoter in a host cell. When it is an RNA, it is preferably a single-stranded RNA.

Since the complex of the present invention does not accompany double-stranded DNA breaks (DSB), genome editing with low toxicity is possible, and the genetic modification method of the present invention can be applied to a wide range of biological materials. Therefore, the cells to be introduced with nucleic acid encoding the above-mentioned nucleic acid converting enzyme complex can encompass cells of any species, from bacterium of *Escherichia coli* and the like which are prokaryotes, cells of microorganism such as yeast and the like which are lower eucaryotes, to cells of vertebrate including mammals such as human and the like, and cells of higher eukaryote such as insect, plant and the like.

A DNA encoding a nucleic acid sequence-recognizing module such as zinc finger motif, TAL effector, PPR motif and the like can be obtained by any method mentioned above for each module. A DNA encoding a sequence-recognizing module of restriction enzyme, transcription factor, RNA polymerase and the like can be cloned by, for example, synthesizing an oligoDNA primer covering a region encoding a desired part of the protein (part containing DNA binding domain) based on the cDNA sequence information thereof, and amplifying by the RT-PCR method using, as a template, the total RNA or mRNA fraction prepared from the protein-producing cells.

A DNA encoding a nucleic acid base converting enzyme and base excision repair inhibitor can also be cloned similarly by synthesizing an oligoDNA primer based on the cDNA sequence information thereof, and amplifying by the RT-PCR method using, as a template, the total RNA or mRNA fraction prepared from the enzyme-producing cells. For example, a DNA encoding PBS2-derived Ugi can be cloned by designing suitable primers for the upstream and downstream of CDS based on the DNA sequence (accession No. J04434) registered in the NCBI/GenBank database, and cloning from PBS2-derived mRNA by the RT-PCR method.

The cloned DNA may be directly used as a DNA encoding a protein, or prepared into a DNA encoding a protein after digestion with a restriction enzyme when desired, or after addition of a suitable linker (e.g., GS linker, GGGAR linker etc.), spacer (e.g., FLAG sequence etc.) and/or a nuclear localization signal (NLS) (each organelle transfer signal when the object double-stranded DNA is mitochondria or chloroplast DNA). It may be further ligated with a DNA encoding a nucleic acid sequence-recognizing module to prepare a DNA encoding a fusion protein.

Alternatively, a DNA encoding a nucleic acid modification enzyme complex may be fused with a DNA encoding a binding domain or a binding partner thereof, or both DNAs may be fused with a DNA encoding a separation intein, whereby the nucleic acid sequence-recognizing conversion module and the nucleic acid modification enzyme complex are translated in a host cell to form a complex. In these cases, a linker and/or a nuclear localization signal can be linked to a suitable position of one of or both DNAs when desired.

A DNA encoding a nucleic acid modification enzyme complex can be obtained by chemically synthesizing the DNA strand, or by connecting synthesized partly overlapping oligoDNA short strands by utilizing the PCR method and the Gibson Assembly method to construct a DNA encoding the full length thereof. The advantage of constructing a full-length DNA by chemical synthesis or a combination of PCR method or Gibson Assembly method is that the codon to be used can be designed in CDS full-length according to the host into which the DNA is introduced. In the expression of a heterologous DNA, the protein expression level is expected to increase by converting the DNA sequence thereof to a codon highly frequently used in the host organism. As the data of codon use frequency in host to be used, for example, the genetic code use frequency database kazusa.or.jp/codon/index.html) disclosed in the home page of Kazusa DNA Research Institute can be used, or documents showing the codon use frequency in each host may be referred to. By reference to the obtained data and the DNA sequence to be introduced, codons showing low use frequency in the host from among those used for the DNA sequence may be converted to a codon coding the same amino acid and showing high use frequency.

An expression vector containing a DNA encoding a nucleic acid modification enzyme complex can be produced, for example, by linking the DNA to the downstream of a promoter in a suitable expression vector.

As the expression vector, *Escherichia coli*-derived plasmids (e.g., pBR322, pBR325, pUC12, pUC13); *Bacillus subtilis*-derived plasmids (e.g., pUB110, pTP5, pC194); yeast-derived plasmids (e.g., pSH19, pSH15); insect cell expression plasmids (e.g., pFast-Bac); animal cell expression plasmids (e.g., pA1-11, pXT1, pRc/CMV, pRc/RSV, pcDNAI/Neo); bacteriophages such as λphage and the like; insect virus vectors such as baculovirus and the like (e.g., BmNPV, AcNPV); animal virus vectors such as retrovirus, vaccinia virus, adenovirus and the like, and the like are used.

As the promoter, any promoter appropriate for a host to be used for gene expression can be used. In a conventional method accompanying DSB, since the survival rate of the host cell sometimes decreases markedly due to the toxicity, it is desirable to increase the number of cells by the start of the induction by using an inductive promoter. However, since sufficient cell proliferation can also be afforded by expressing the nucleic acid-modifying enzyme complex of the present invention, a constituent promoter can also be used without limitation.

For example, when the host is an animal cell, SRα promoter, SV40 promoter, LTR promoter, CMV (cytomegalovirus) promoter, RSV (Rous sarcoma virus) promoter, MoMuLV (Moloney mouse leukemia virus) LTR, HSV-TK (simple herpes virus thymidine kinase) promoter and the like are used. Of these, CMV promoter, SRα promoter and the like are preferable.

When the host is *Escherichia coli*, trp promoter, lac promoter, recA promoter, $\lambda P_L$ promoter, lpp promoter, T7 promoter and the like are preferable.

When the host is genus *Bacillus*, SPO1 promoter, SPO2 promoter, penP promoter and the like are preferable.

When the host is a yeast, Gal1/10 promoter, PHO5 promoter, PGK promoter, GAP promoter, ADH promoter and the like are preferable.

When the host is an insect cell, polyhedrin promoter, P10 promoter and the like are preferable.

When the host is a plant cell, CaMV35S promoter, CaMV19S promoter, NOS promoter and the like are preferable.

As the expression vector, besides those mentioned above, one containing enhancer, splicing signal, terminator, polyA addition signal, a selection marker such as drug resistance gene, auxotrophic complementary gene and the like, replication origin and the like on demand can be used.

An RNA encoding a nucleic acid modification enzyme complex can be prepared by, for example, transcription to mRNA in a vitro transcription system known per se by using a vector containing a DNA encoding each protein as a template.

The complex of the present invention can be intracellularly expressed by introducing an expression vector containing a DNA encoding a nucleic acid modification enzyme complex, and culturing the host cell.

As the host, genus *Escherichia*, genus *Bacillus*, yeast, insect cell, insect, animal cell and the like are used.

As the genus *Escherichia, Escherichia coli* K12.DH1 [Proc. Natl. Acad. Sci. USA, 60, 160 (1968)], *Escherichia coli* JM103 [Nucleic Acids Research, 9, 309 (1981)], *Escherichia coli* JA221 [Journal of Molecular Biology, 120, 517 (1978)], *Escherichia coli* HB101 [Journal of Molecular Biology, 41, 459 (1969)], *Escherichia coli* C600 [Genetics, 39, 440 (1954)] and the like are used.

As the genus *Bacillus, Bacillus subtilis* MI114 [Gene, 24, 255 (1983)], *Bacillus subtilis* 207-21 [Journal of Biochemistry, 95, 87 (1984)] and the like are used.

As the yeast, Saccharomyces cerevisiae AH22, $AH22R^-$, NA87-11A, DKD-5D, 20B-12, Schizosaccharomyces pombe NCYC1913, NCYC2036, Pichia pastoris KM71 and the like are used.

As the insect cell when the virus is AcNPV, cells of cabbage armyworm larva-derived established line (Spodoptera frugiperda cell; Sf cell), MG1 cells derived from the mid-intestine of Trichoplusia ni, High Five™ cells derived from an egg of Trichoplusia ni, Mamestra brassicae-derived cells, Estigmena acrea-derived cells and the like are used. When the virus is BmNPV, cells of Bombyx mori-derived established line (Bombyx mori N cell; BmN cell) and the like are used as insect cells. As the Sf cell, for example, Sf9 cell (ATCC CRL1711), Sf21 cell [all above, In Vivo, 13, 213-217 (1977)] and the like are used.

As the insect, for example, larva of Bombyx mori, Drosophila, cricket and the like are used [Nature, 315, 592 (1985)].

As the animal cell, cell lines such as monkey COS-7 cell, monkey Vero cell, CHO cell, dhfr gene-deficient CHO cell, mouse L cell, mouse AtT-20 cell, mouse myeloma cell, rat GH3 cell, human FL cell, human fetal kidney-derived cells (e.g., HEK293 cell) and the like, pluripotent stem cells such as iPS cell, ES cell and the like of human and other mammals, and primary cultured cells prepared from various tissues are used. Furthermore, zebrafish embryo, Xenopus oocyte and the like can also be used.

As the plant cell, suspend cultured cells, callus, protoplast, leaf segment, root segment and the like prepared from various plants (e.g., grain such as rice, wheat, corn and the like, product crops such as tomato, cucumber, egg plant and the like, garden plants such as carnation, Eustoma russellianum and the like, experiment plants such as tobacco, *Arabidopsis thaliana* and the like, and the like) are used.

All the above-mentioned host cells may be haploid (monoploid), or polyploid (e.g., diploid, triploid, tetraploid and the like).

An expression vector can be introduced by a known method (e.g., lysozyme method, competent method, PEG method, $CaCl_2$ coprecipitation method, electroporation method, the microinjection method, the particle gun method, lipofection method, *Agrobacterium* method and the like) according to the kind of the host.

*Escherichia coli* can be transformed according to the methods described in, for example, Proc. Natl. Acad. Sci. USA, 69, 2110 (1972), Gene, 17, 107 (1982) and the like.

The genus *Bacillus* can be introduced into a vector according to the methods described in, for example, Molecular & General Genetics, 168, 111 (1979) and the like.

A yeast can be introduced into a vector according to the methods described in, for example, Methods in Enzymology, 194, 182-187 (1991), Proc. Natl. Acad. Sci. USA, 75, 1929 (1978) and the like.

An insect cell and an insect can be introduced into a vector according to the methods described in, for example, Bio/Technology, 6, 47-55 (1988) and the like.

An animal cell can be introduced into a vector according to the methods described in, for example, Cell Engineering additional volume 8, New Cell Engineering Experiment Protocol, 263-267 (1995) (published by Shujunsha), and Virology, 52, 456 (1973).

A cell introduced with a vector can be cultured according to a known method according to the kind of the host.

For example, when *Escherichia coli* or genus *Bacillus* is cultured, a liquid medium is preferable as a medium to be used for the culture. The medium preferably contains a carbon source, nitrogen source, inorganic substance and the like necessary for the growth of the transformant. Examples of the carbon source include glucose, dextrin, soluble starch, sucrose and the like; examples of the nitrogen source include inorganic or organic substances such as ammonium salts, nitrate salts, corn steep liquor, peptone, casein, meat extract, soybean cake, potato extract and the like; and examples of the inorganic substance include calcium chloride, sodium dihydrogen phosphate, magnesium chloride and the like. The medium may contain yeast extract, vitamins, growth promoting factor and the like. The pH of the medium is preferably about 5-about 8.

As a medium for culturing Escherichia coli, for example, M9 medium containing glucose, casamino acid [Journal of Experiments in Molecular Genetics, 431-433, Cold Spring Harbor Laboratory, New York 1972] is preferable. Where necessary, for example, agents such as 3β-indolylacrylic acid may be added to the medium to ensure an efficient function of a promoter. *Escherichia coli* is cultured at generally about 15-about 43° C. Where necessary, aeration and stirring may be performed.

The genus *Bacillus* is cultured at generally about 30-about 40° C. Where necessary, aeration and stirring may be performed.

Examples of the medium for culturing yeast include Burkholder minimum medium [Proc. Natl. Acad. Sci. USA, 77, 4505 (1980)], SD medium containing 0.5% casamino acid [Proc. Natl. Acad. Sci. USA, 81, 5330 (1984)] and the like. The pH of the medium is preferably about 5-about 8. The culture is is performed at generally about 20° C.-about 35° C. Where necessary, aeration and stirring may be performed.

As a medium for culturing an insect cell or insect, for example, Grace's Insect Medium [Nature, 195, 788 (1962)] containing an additive such as inactivated 10% bovine serum and the like as appropriate and the like are used. The pH of the medium is preferably about 6.2-about 6.4. The culture is performed at generally about 27° C. Where necessary, aeration and stirring may be performed.

As a medium for culturing an animal cell, for example, minimum essential medium (MEM) containing about 5-about 20% of fetal bovine serum [Science, 122, 501 (1952)], Ham's F12 medium, Dulbecco's modified Eagle medium (DMEM) [Virology, 8, 396 (1959)], RPMI 1640 medium [The Journal of the American Medical Association, 199, 519 (1967)], 199 medium [Proceeding of the Society for the Biological Medicine, 73, 1 (1950)] and the like are used. The pH of the medium is preferably about 6-about 8. The culture is performed at generally about 30° C.-about 40° C. Where necessary, aeration and stirring may be performed.

As a medium for culturing a plant cell, for example, MS medium, LS medium, B5 medium and the like are used. The pH of the medium is preferably about 5-about 8. The culture is performed at generally about 20° C.-about 30° C. Where necessary, aeration and stirring may be performed.

The culture period is not particularly limited as long as it is at least the period necessary for the targeted site of the double-stranded DNA to be modified, and can be appropriately selected according to the host cell. To avoid undesirable off-target mutation, preferably, the culture is not performed beyond a period sufficient to modify the targeted site. The timing and duration of the low temperature culture when performing the step of culturing at a low temperature at least temporarily is as described above.

As mentioned above, nucleic acid modification enzyme complex can be expressed intracellularly.

An RNA encoding a nucleic acid modification enzyme complex can be introduced into a host cell by microinjection method, lipofection method and the like. RNA introduction can be performed once or repeated multiple times (e.g., 2-5 times) at suitable intervals.

When a complex of a nucleic acid sequence-recognizing module and a nucleic acid base converting enzyme is expressed by an expression vector or RNA molecule introduced into the cell, the nucleic acid sequence-recognizing module specifically recognizes and binds to a target nucleotide sequence in the double-stranded DNA (e.g., genomic DNA) of interest and, due to the action of the nucleic acid base converting enzyme linked to the nucleic acid sequence-recognizing module, base conversion occurs in the sense strand or antisense strand of the targeted site (whole or partial target nucleotide sequence or appropriately adjusted within several hundred bases including the vicinity thereof) and a mismatch occurs in the double-stranded DNA (e.g., when cytidine deaminase such as PmCDA1, AID and the like is used as a nucleic acid base converting enzyme, cytosine on the sense strand or antisense strand at the targeted site is converted to uracil to cause U:G or G:U mismatch). When the mismatch is not correctly repaired, and when repaired such that a base of the opposite strand forms a pair with a base of the converted strand (T-A or A-T in the above-mentioned example), or when other nucleotide is further substituted (e.g., U→A, G) or when one to several dozen bases are deleted or inserted during repair, various mutations are introduced. By using inhibitors of base excision repair in combination, the BER mechanism in cells is inhibited, the frequency of repair error is increased, and mutation introduction efficiency can be improved.

As for zinc finger motif, production of many actually functionable zinc finger motifs is not easy, since production efficiency of a zinc finger that specifically binds to a target nucleotide sequence is not high and selection of a zinc finger having high binding specificity is complicated. While TAL effector and PPR motif have a high degree of freedom of target nucleic acid sequence recognition as compared to zinc finger motif, a problem remains in the efficiency since a large protein needs to be designed and constructed every time according to the target nucleotide sequence.

In contrast, since the CRISPR-Cas system recognizes the object double-stranded DNA sequence by a guide RNA complementary to the target nucleotide sequence, any sequence can be targeted by simply synthesizing an oligoDNA capable of specifically forming a hybrid with the target nucleotide sequence.

Therefore, in a more preferable embodiment of the present invention, a CRISPR-Cas system wherein at least one DNA cleavage ability of Cas is inactivated (CRISPR-mutant Cas) is used as a nucleic acid sequence-recognizing module.

FIG. 1 is a schematic showing of the genome editing plasmid of the present invention using CRISPR-mutant Cas as a nucleic acid sequence-recognizing module.

The nucleic acid sequence-recognizing module of the present invention using CRISPR-mutant Cas is provided as a complex of an RNA molecule consisting of a guide RNA (gRNA) complementary to the target nucleotide sequence and tracrRNA necessary for recruiting mutant Cas protein, and a mutant Cas protein.

The Cas protein to be used in the present invention is not particularly limited as long as it belongs to the CRISPR system, and preferred is Cas9. Examples of Cas9 include, but are not limited to, *Streptococcus pyogenes*-derived Cas9 (SpCas9), *Streptococcus thermophilus*-derived Cas9 (StCas9) and the like. Preferred is SpCas9. As a mutant Cas to be used in the present invention, any of Cas wherein the cleavage ability of the both strands of the double-stranded DNA is inactivated and one having nickase activity wherein at least one cleavage ability of one strand alone is inactivated can be used. For example, in the case of SpCas9, a D10A mutant wherein the 10th Asp residue is converted to an Ala residue and lacking cleavage ability of a strand opposite to the strand forming a complementary strand with a guide RNA, or H840A mutant wherein the 840th His residue is converted to an Ala residue and lacking cleavage ability of strand complementary to guide RNA, or a double mutant thereof can be used, and other mutant Cas can be used similarly.

A nucleic acid base converting enzyme and base excision repair inhibitor are provided as a complex with mutant Cas by a method similar to the coupling scheme with the above-mentioned zinc finger and the like. Alternatively, a nucleic acid base converting enzyme and/or base excision repair inhibitor and mutant Cas can also be bound by utilizing RNA aptamers MS2F6, PP7 and the like and RNA scaffold by binding proteins thereto. Guide RNA forms a complementary strand with the target nucleotide sequence, mutant Cas is recruited by the tracrRNA attached and mutant Cas recognizes DNA cleavage site recognition sequence PAM (protospacer adjacent motif) (when SpCas9 is used, PAM is 3 bases of NGG (N is any base), and, theoretically, can target any position on the genome). One or both DNAs cannot be cleaved, and, due to the action of the nucleic acid base converting enzyme linked to the mutant Cas, nucleic acid base conversion occurs in the targeted site (appropriately adjusted within several hundred bases including whole or partial target nucleotide sequence) and a mismatch occurs in the double-stranded DNA. Due to the error of the BER system of the cell to be repaired, various mutations are introduced.

When CRISPR-mutant Cas is used as a nucleic acid sequence-recognizing module, CRISPR-mutant Cas is desirably introduced, in the form of a nucleic acid encoding nucleic acid modification enzyme complex, into a cell having a double-stranded DNA of interest, similar to when zinc finger and the like are used as a nucleic acid sequence-recognizing module.

A DNA encoding Cas can be cloned by a method similar to the above-mentioned method for a DNA encoding a base excision repair inhibitor, from a cell producing the enzyme. A mutant Cas can be obtained by introducing a mutation to convert an amino acid residue of the part important for the DNA cleavage activity (e.g., 10th Asp residue and 840th His residue for Cas9, though not limited thereto) to other amino acid, into a DNA encoding cloned Cas, by a site specific mutation induction method known per se.

Alternatively, a DNA encoding mutant Cas can also be constructed as a DNA having codon usage suitable for expression in a host cell to be used, by a method similar to those mentioned above for a DNA encoding a nucleic acid sequence-recognizing module and a DNA encoding a DNA glycosylase, and by a combination of chemical synthesis or PCR method or Gibson Assembly method. For example, CDS sequence and amino acid sequence optimized for the expression of SpCas9 in eukaryotic cells are shown in SEQ ID NOs: 3 and 4. In the sequence shown in SEQ ID NO: 3, when "A" is converted to "C" in base No. 29, a DNA encoding a D10A mutant can be obtained, and when "CA" is converted to "GC" in base No. 2518-2519, a DNA encoding an H840A mutant can be obtained.

A DNA encoding a mutant Cas and a DNA encoding a nucleic acid base converting enzyme may be linked to allow for expression as a fusion protein, or designed to be separately expressed using a binding domain, intein and the like, and form a complex in a host cell via protein-protein interaction or protein ligation. Alternatively, a design may be employed in which a DNA encoding mutant Cas and a DNA encoding a nucleic acid base converting enzyme are each split into two fragments at suitable split site, either fragments are linked to each other directly or via a suitable linker to express a nucleic acid-modifying enzyme complex as two partial complexes, which are associated and refolded in the cell to reconstitute functional mutant Cas having a particular nucleic acid sequence recognition ability, and a functional nucleic acid base converting enzyme having a nucleic acid base conversion reaction catalyst activity is reconstituted when the mutant Cas is bonded to the target nucleotide sequence. For example, a DNA encoding the N-terminal side fragment of mutant Cas9 and a DNA encoding the C-terminal side fragment of mutant Cas are respectively prepared by the PCR method by using suitable primers; a DNA encoding the N-terminal side fragment of a nucleic acid base converting enzyme and a DNA encoding the C-terminal side fragment of a nucleic acid base converting enzyme are prepared in the same manner; for example, the DNAs encoding the N-terminal side fragments are linked to each other, and the DNAs encoding the C-terminal side fragments are linked to each other by a conventional method, whereby a DNA encoding two partial complexes can be produced. Alternatively, a DNA encoding the N-terminal side fragment of mutant Cas and a DNA encoding the C-terminal side fragment of a nucleic acid base converting enzyme are linked; and a DNA encoding the N-terminal side fragment of a nucleic acid base converting enzyme and a DNA encoding the C-terminal side fragment of mutant Cas are linked, whereby a DNA encoding two partial complexes can also be produced. Respective partial complexes may be linked to allow for expression as a fusion protein, or designed to be separately expressed using a binding domain, intein and the like, and form a complex in a host cell via protein-protein interaction or protein ligation. Two partial complexes may be linked to be expressed as a fusion protein. The split site of the mutant Cas is not particularly limited as long as the two split fragments can be reconstituted such that they recognize and bind to the target nucleotide sequence, and it may be split at one site to provide N-terminal side fragment and C-terminal side fragment, or not less than 3 fragments obtained by splitting at two or more sites may be appropriately linked to give two fragments. The three-dimensional structures of various Cas proteins are known, and those of ordinary skill in the art can appropriately select the split site based on such information. For example, since the region consisting of the 94th to the 718th amino acids from the N terminus of SpCas9 is a domain (REC) involved in the recognition of the target nucleotide sequence and guide RNA, and the region consisting of the 1099th amino acid to the C-terminal amino acid is the domain (PI) involved in the interaction with PAM, the N-terminal side fragment and the C-terminal side fragment can be split at any site in REC domain or PI domain, preferably in a region free of a structure (e.g., between 204th and 205th amino acid from the N-terminal (204.. 205), between 535th and 536th amino acids from the N-terminal (535.. 536) and the like) (see, for example, Nat Biotechnol. 33(2): 139-142 (2015)). A combination of a DNA encoding a base excision repair inhibitor and a DNA encoding a mutant Cas and/or a DNA encoding a nucleic acid base converting enzyme can also be designed in the same manner as described above.

The obtained DNA encoding a mutant Cas and/or a nucleic acid base converting enzyme and/or base excision repair inhibitor can be inserted into the downstream of a promoter of an expression vector similar to the one mentioned above, according to the host.

On the other hand, a DNA encoding guide RNA and tracrRNA can be obtained by designing an oligoDNA sequence linking a coding sequence of crRNA sequence containing a nucleotide sequence complementary to the target nucleotide sequence (e.g., when FnCpf1 is recruited as Cas, crRNA containing SEQ ID NO: 20; AAUUUCUACUGUUGUAGAU at the 5'-side of the complementary nucleotide sequence can be used, and underlined sequences form base pairs to take a stem-loop structure), or a crRNA coding sequence and, as necessary, a known tracrRNA coding sequence (e.g., as tracrRNA coding sequence when Cas9 is recruited as Cas, gttttagagctagaaatagcaagttaaaataaggctagtccgttatcaacttgaaaaagtggc accgagtcggtggtgctttt; SEQ ID NO: 9) and chemically synthesizing using a DNA/RNA synthesizer. While a DNA encoding guide RNA and tracrRNA can also be inserted into an expression vector similar to the one mentioned above, according to the host. As the promoter, pol III system promoter (e.g., SNR6, SNR52, SCR1, RPR1, U6, H1 promoter etc.) and terminator (e.g., $T_6$ sequence) are preferably used.

An RNA encoding mutant Cas and/or a nucleic acid base converting enzyme and/or base excision repair inhibitor can be prepared by, for example, transcription to mRNA in vitro transcription system known per se by using a vector encoding the above-mentioned mutant Cas and/or a nucleic acid base converting enzyme and/or base excision repair inhibitor as a template.

Guide RNA-tracrRNA can be obtained by designing an oligoDNA sequence linking a sequence complementary to the target nucleotide sequence and known tracrRNA sequence and chemically synthesizing using a DNA/RNA synthesizer.

A DNA or RNA encoding mutant Cas and/or a nucleic acid base converting enzyme and/or base excision repair inhibitor, guide RNA-tracrRNA or a DNA encoding same can be introduced into a host cell by a method similar to the above, according to the host.

Since conventional artificial nuclease accompanies Double-stranded DNA breaks (DSB), inhibition of growth and cell death assumedly caused by disordered cleavage of chromosome (off-target cleavage) occur by targeting a sequence in the genome. The effect thereof is particularly fatal for many microorganisms and prokaryotes, and prevents applicability. In the method of the present invention, cytotoxicity is drastically reduced as compared to a method using a conventional artificial nuclease since mutation introduction is performed not by DNA cleavage but by nucleic acid base conversion reaction on DNA.

When sequence-recognizing modules are produced corresponding to the adjacent multiple target nucleotide sequences, and simultaneously used, the mutation introduction efficiency can increase more than using a single nucleotide sequence as a target. As the effect thereof, similarly mutation induction is realized even when both target nucleotide sequences partly overlap or when the both are apart by about 600 bp. It can occur both when the target nucleotide sequences are in the same direction (target nucleotide sequences are present on the same strand), and when they are opposed (target nucleotide sequence is present on each strand of double-stranded DNA).

Since the genome editing technique of the present invention shows extremely high mutation introduction efficiency, modification of multiple DNA regions at completely different positions as targets can be performed. Therefore, in one preferable embodiment of the present invention, two or more kinds of nucleic acid sequence-recognizing modules that specifically bind to different target nucleotide sequences (which may be present in one object gene, or two or more different object genes, which object genes may be present on the same chromosome or different chromosomes) can be used. In this case, each one of these nucleic acid sequence-recognizing modules, a nucleic acid base converting enzyme and a base excision repair inhibitor form a nucleic acid-modifying enzyme complex. Here, a common nucleic acid base converting enzyme and a base excision repair inhibitor can be used. For example, when CRISPR-Cas system is used as a nucleic acid sequence-recognizing module, a common complex of a Cas protein, a nucleic acid base converting enzyme and a base excision repair inhibitor (including fusion protein) are used, and two or more kinds of chimeric RNAs of tracrRNA and each of two or more guide RNAs that respectively form a complementary strand with a different target nucleotide sequence are produced and used as guide RNA-tracrRNAs. On the other hand, when zinc finger motif, TAL effector and the like are used as nucleic acid sequence-recognizing modules, for example, a nucleic acid base converting enzyme and base excision repair inhibitor can be fused with a nucleic acid sequence-recognizing module that specifically binds to a different target nucleotide.

To express the nucleic acid-modifying enzyme complex of the present invention in a host cell, as mentioned above, an expression vector containing a DNA encoding the nucleic acid-modifying enzyme complex, or an RNA encoding the nucleic acid-modifying enzyme complex is introduced into a host cell. For efficient introduction of mutation, it is desirable to maintain an expression of nucleic acid-modifying enzyme complex of a given level or above for not less than a given period. From such aspect, it is ensuring to introduce an expression vector (plasmid etc.) autonomously replicatable in a host cell. However, since the plasmid etc. are foreign DNAs, they are preferably removed rapidly after successful introduction of mutation. Therefore, though subject to change depending on the kind of host cell and the like, for example, the introduced plasmid is desirably removed from the host cell after a lapse of 6 hr-2 days from the introduction of an expression vector by using various plasmid removal methods well known in the art.

Alternatively, as long as expression of a nucleic acid-modifying enzyme complex, which is sufficient for the introduction of mutation, is obtained, it is preferable to introduce mutation into the object double-stranded DNA by transient expression by using an expression vector or RNA without autonomous replicatability in a host cell (e.g., vector etc. lacking replication origin that functions in host cell and/or gene encoding protein necessary for replication).

The present invention is explained in the following by referring to Examples, which are not to be construed as limitative.

EXAMPLES

In the below-mentioned Examples, experiments were performed as follows.

<Cell Line•Culture•Transformation•Expression Induction>

CHO-K1 adherent cell derived from Chinese hamster ovary was used. The cell was cultured in a hamF12 medium (Life Technologies, Carlsbad, CA, USA) supplemented with 10% fetal bovine serum (Biosera, Nuaille, France) and 100 μg/mL penicillin-streptomycin (Life Technologies, Carlsbad, CA, USA). The cells were incubated under humidified 5% $CO_2$ atmosphere at 37° C. For transfection, a 24 well plate was used and the cells were seeded at $0.5\times10^5$ cells per well and cultured for one day. According to the manufacturer's instructions, 1.5 μg of plasmid and 2 μL of lipofectamine 2000 (Life Technologies, Carlsbad, CA, USA) were transfected into the cells. After 5 hr from the transfection, the medium was exchanged with hamF12 medium containing 0.125 mg/mL G418 (InvivoGen, San Diego, Calf., USA) and the cells were incubated for 7 days. Thereafter, the cells were used for the calculation of the following mutation introduction efficiency.

The step of culturing at a low temperature temporarily included transfection similar to the above-mentioned, medium exchange with hamF12 medium containing 0.125 mg/mL G418 at 5 hr after the transfection medium, continuous overnight culture at 25° C., and culturing for 2 days at 37° C. Thereafter, the cells were used for the following calculation of the mutation introduction efficiency.

<Calculation of Mutation Introduction Efficiency>

Figure 2:
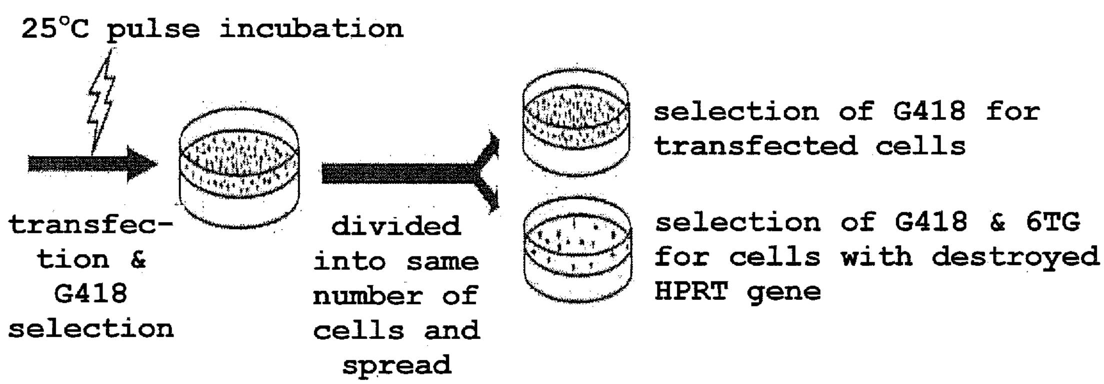
FIG. 2 is a schematic showing of the evaluation method of the mutation introduction efficiency.

The outline of the calculation of the mutation introduction efficiency is shown in FIG. 2. HPRT (Hypoxanthine-guanine phosphoribosyltransferase) is one of the purine metabolic enzymes, and the cells with destroyed HPRT gene acquires resistance to 6-TG (6-thioguanine). To calculate mutation introduction efficiency of HPRT gene, the cells were detached from plastic by using trypsin-EDTA (Life Technologies, Carlsbad, CA, USA) and 100-500 cells were spread on a dish containing hamF12 medium containing G418 or G418+5 g/mL 6-TG (Tokyo Chemical Industry, Tokyo, Japan). Seven days later, the number of resistant colonies was counted. The mutation introduction efficiency was calculated as a ratio of 6TG resistant colonies to the G418 resistant colonies.

<Sequence Analysis>

For sequence analysis, G418 and 6TG resistant colonies were treated with trypsin and pelletized by centrifugation. According to manufacturer's instructions, genomic DNA was extracted from the pellets by using NucleoSpin Tissue XS kit (Macherey-Nagel, Duren, Germany). PCR fragments containing the targeted site of HPRT was amplified from genomic DNA by using the forward primer (ggctacatagagggatcctgtgtca; SEQ ID NO: 18) and the reverse primer (acagtagctcttcagtctgataaaa; SEQ ID NO: 19). The PCR product was TA cloned into *Escherichia coli* (*E. coli*) vector and analyzed by the Sanger method.

<Nucleic Acid Operation>

DNA was processed or constructed by any of PCR method, restriction enzyme treatment, ligation, Gibson Assembly method, and artificial chemical synthesis. The plasmid was amplified with *Escherichia coli* strain XL-10 gold or DH5α and introduced into the cells by the lipofection method.

<Construct>

The outline of the genome editing plasmid vector used in the Example is shown in FIG. 1. Using pcDNA3.1 vector as a base, a vector used for gene transfer by transfection into CHO cells was constructed. A nuclear localization signal (ccc aag aag aag agg aag gtg; SEQ ID NO: 11 (PKKKRKV; encoding SEQ ID NO: 12)) which was added to *Streptococcus pyogenes*-derived Cas9 gene ORF having a codon optimized for eucaryon expression (SEQ ID NO: 3 (encoding SEQ ID NO: 4)), the resulting construct was ligated to the downstream of a CMV promoter via a linker sequence, a deaminase gene (Petromyzon marinus Petromyzon marinus-derived PmCDA1) ORF having a codon optimized for human cell expression (SEQ ID NO: 1 (encoding SEQ ID NO: 2)) was added thereto, and then the obtained product was expressed as a fusion protein. In addition, a construct for fusion expression of Ugi gene (PBS2-derived Ugi was codon-optimized for eukaryotic cell expression: SEQ ID NO: 5 (encoding SEQ ID NO: 6)) was also produced. A drug resistant gene (NeoR: G418 resistant gene) was also ligated via a sequence encoding 2A peptide (gaa ggc agg gga agc ctt ctg act tgt ggg gat gtg gaa gaa aac cct ggt cca; SEQ ID NO: 13 (encoding EGRGSLLTCGDVEENPGP; SEQ ID NO: 14)). As the linker sequence, 2xGS linker (two repeats of ggt gga gga ggt tct; SEQ ID NO: 15 (encoding GGGGS; SEQ ID NO: 16)) was used. As the terminator, SV40 poly A signal terminator (SEQ ID NO: 17) was ligated.

In Cas9, mutant Cas9 (nCas9) into which a mutation to convert the 10th aspartic acid to alanine (D10A, corresponding DNA sequence mutation a29c) was introduced and mutant Cas9 (dCas9) into which a mutation to convert the 840th histidine to alanine (H840A, corresponding DNA sequence mutation ca2518 gc) was further introduced were used to remove cleavage ability of each or both sides of DNA strand.

gRNA was placed between the H1 promoter (SEQ ID NO: 10) and the poly T signal (tttttt) as a chimeric structure with tracrRNA (derived from *Streptococcus pyogenes*; SEQ ID NO: 9) and incorporated into a plasmid vector for expressing the above-mentioned deaminase gene and the like. As the gRNA-targeting base sequence, the 16th-34th sequence (ccgagatgtcatgaaagaga; SEQ ID NO: 7) (site 1) from the start point of exon3 of the HPRT gene, and a complementary strand sequence (ccatgacggaatcggtcggc; SEQ ID NO: 8) (site 2R) to the −15th-3rd sequence from the start point of exon1 of the HPRT gene were used. They were introduced into the cell, expressed in the cells to form a complex of gRNA-tracrRNA and Cas9-PmCDA1 or Cas9-PmCDA1-Ugi.

Example 1 Various Genome Editing Plasmids and Evaluation of Mutation Introduction Efficiency by Conditions The evaluation results of various genome editing plasmids and mutation introduction efficiency by conditions are shown in Table 1. In Example 1, site 1 (SEQ ID NO: 7) was used as the gRNA-targeting base sequence for all those not described as site 2R.

TABLE 1

| | Modifier plasmid | Transformants 6-TG resisntant | mutation frequency |
|---|---|---|---|
| | Cas | 341<br>328 | 96.2% |
| | nCas (D10A)-2A-Neo | 4745<br>3 | 0.06% |
| | nCas-PmCDA1-2A-Neo | 282<br>101 | 35.9% |
| | dCas-PmCDA1-2A-Neo | 384<br>8 | 2.08% |
| | dCas-2A-Neo site1 | 8066<br>0 | 0% |
| | dCas-2A-Neo site2R | 6241<br>0 | 0% |
| | Neo only | 15180<br>0 | 0% |
| +25° C. pulse | dCas-2A-Neo | 8900<br>0 | 0% |
| | nCas-PmCDA1-2A-Neo | 480<br>297 | 61.9% |
| | dCas-PmCDA1-2A-Neo | 240<br>30 | 12.5% |
| +Ugi | nCas-PmCDA1-2A-Neo | 723<br>658 | 91.0% |
| | dCas-PmCDA1-2A-Neo | 823<br>709 | 86.2% |

A plasmid using nCas9 as mutant Cas9 (nCas-PmCDA1-2A-Neo) showed mutation introduction efficiency of 35.9%, and a plasmid using dCas9 as mutant Cas9 mutant (dCas-PmCDA1-2A-Neo) showed mutation introduction efficiency of 2.08%. On the other hand, in cases using a plasmid with Ugi ligated to PmCDA1, a plasmid using nCas9 as mutant Cas9 (+Ugi nCas-PmCDA1-2A-Neo) showed mutation introduction efficiency of 91.0%, and a plasmid using dCas9 as mutant Cas9 (+Ugi dCas-PmCDA1-2A-Neo) showed mutation introduction efficiency of 86.2%. Therefore, it was shown that mutation introduction efficiency is significantly improved by fusion expression of Ugi protein which inhibits repair of deaminated bases, and particularly, one using dCas9 showed a striking increase in the mutation introduction efficiency improving effect by the combined use of Ugi. In Table 1, Cas shows a plasmid using Cas9 without introduction of mutation, nCas(D10A)-2A-Neo, dCas-2A-Neo site 1 and dCas-2A-Neo site 2R show plasmids without ligation of a nucleic acid base converting enzyme, and they were each used as a control.

In addition, it was shown that the cells cultured temporarily (overnight) at a low temperature of 25° C. (+25° C. pulse) after transfection and using any of nCas9 (nCas-PmCDA1-2A-Neo) and dCas9 (dCas-PmCDA1-2A-Neo) exhibit significantly improved mutation introduction efficiency (61.9% and 12.5%, respectively). In Table 1, dCas-2A-Neo shows a plasmid without fusion with nucleic acid base converting enzyme and used as a control.

From the above, it was shown that, according to the genome editing technique of the present invention, the mutation introduction efficiency is strikingly improved as compared to the conventional genome editing techniques using nucleic acid base converting enzymes.

Example 2 Analysis of Mutation Introduction Pattern

Figure 3:
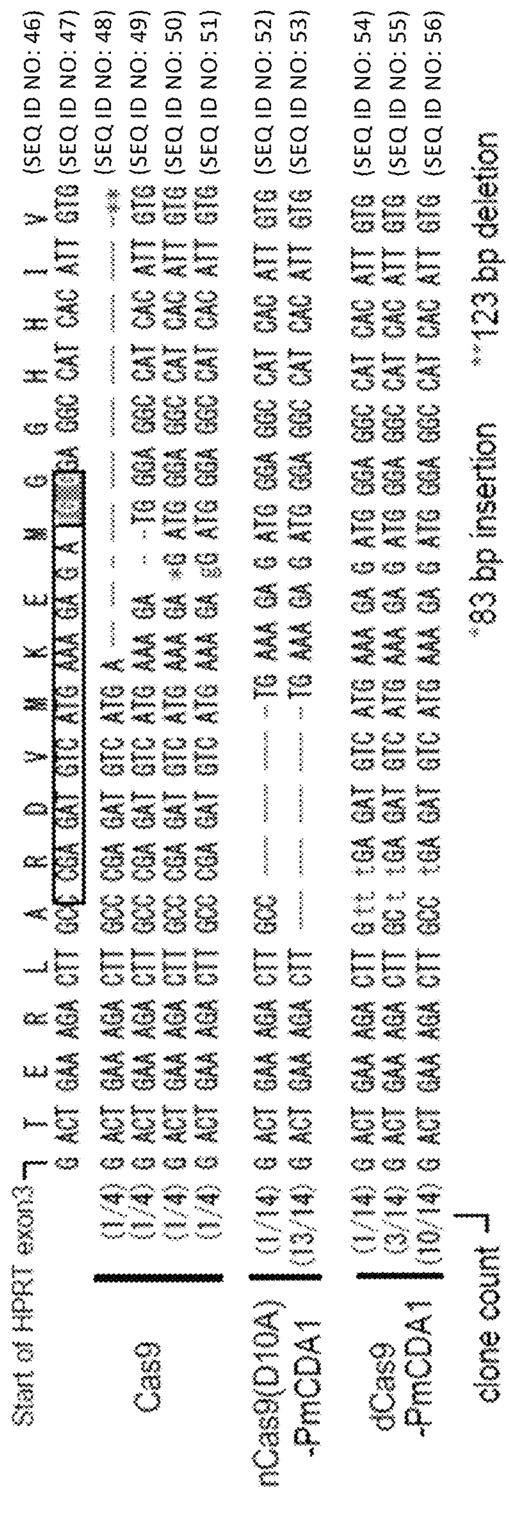
FIG. 3 shows the analysis results of the mutation pattern of the target gene region in the obtained mutant populations.

Genome DNA was extracted from the obtained mutation introduction colonies, the target region of the HPRT gene was amplified by PCR, TA cloning was performed, and sequence analysis was performed. The results are shown in FIG. 3. The editing vectors used were Cas9, nCas9(D10A)-PmCDA1 and dCas9-PmCDA1, the base excision repair inhibitor was not expressed, and the colonies from the cells cultured at 37° C. were used. In the Figure, TGG enclosed in a black box shows PAM sequence.

In Cas9 free of introduction of mutation, large deletions and insertions centered on directly above the PAM sequence were observed. On the other hand, in nCas9 (D10A)-PmCDA1, a small scale deletion of about dozen bases was observed, and the region thereof contained a deamination target base. In dCas9-PmCDA1, a mutation from C to T was observed at 19 to 21 bases upstream of the PAM sequence, and a single base pinpoint mutation was introduced in 10 clones in total 14 clones subjected to sequence analysis.

From the above, it was shown that pinpoint mutation introduction is possible even when a genome editing technique using a nucleic acid base converting enzyme is applied to mammalian cells.

Example 3 Study Using Other Mammalian Cell

Using HEK293T cell, which is derived from human fetal kidney, mutation introduction efficiency was evaluated. The same vector as in Example 1 was used as a vector except that the gRNA target base sequence was the sequence of the EMX1 gene (shown in SEQ ID NO: 21) described in "Tsai S. Q. et al., (2015) Nat Biotechnol., 33(2): 187-197" and the off-target candidate sequences 1 to 4 (respectively correspond to the sequences of Emx 1 off target 1-Emx 1 off target 4 in Tables 2, 3 and shown in SEQ ID NOs: 22-25). The vector was introduced into HEK293T cells by transfection. Without selection of the cells, the whole cells were recovered two days later and genomic DNA was extracted. Culture conditions other than cell selection and period up to total cell recovery and transfection conditions were the same as those of the above-mentioned CHO-K1 cells. Then, according to the method described in "Nishida K. et al. (2016) Science, 6: 353(6305)", the regions containing respective targets were amplified by PCR using the primers shown in Table 2, and mutation introduction pattern was analyzed using a next-generation sequencer. The results are shown in Table 3. In the Table, the number under the sequence shows a substitution rate (%) of the nucleotide.

TABLE 2

| target name | SEQ ID NO: | Primer name | Primer sequence (5'→3') |
|---|---|---|---|
| Emxl | 26 | TA501 EMX 1st-3 | GTAGTCTGGCTGTCACAGGCCATACTCTTCCACAT |
| | 27 | TA575 EMX 1st-6 | GTGGGTGACCCACCCAAGCAGCAGGCTCTCCACCA |
| | 28 | TA576 EMX 2nd-3 | TCTTTCCCTACACGACGCTCTTCCGATCTACTTAGCTGGAGTGTGGAGGCTATCTTGGC |
| | 29 | TA410 EMX 2nd-2 | GTGACTGGAGTTCAGACGTGTGCTCTTCCGATCTGGCTAGGGACTGGCCAGAGTCCAGC |
| Emxl off target 1 | 30 | TA502 EMX-off1 1st-3 | CTGCCCATATCCACCACAAGCAAGTTAGTCATCAA |
| | 31 | TA412 EMX-off1 1st-2 | AATCAAAATCTCTATGTGTGGGGCACAGGG |
| | 32 | TA413 EMX-off1 2nd-1 | TCTTTCCCTACACGACGCTCTTCCGATCTCATTGGCTAGAATTCAGACTTCAAG |
| | 33 | TA414 EMX-off1 2nd-2 | GTGACTGGAGTTCAGACGTGTGCTCTTCCGATCTATGAGGGAGATGTACTCTCAAGTGA |
| Emxl off target 2 | 34 | TA503 EMX-off2 1st-3 | CATGTTCCCTCACCCTTGGCATCTACACACTTTCT |
| | 35 | TA416 EMX-off2 1st-2 | TAGTTTACCCTGAGGCAATATCTGACTCCA |
| | 36 | TA417 EMX-off2 2nd-1 | TCTTTCCCTACACGACGCTCTTCCGATCTTCATTTTCAAATGCCTATTGAGCGG |
| | 37 | TA418 EMX-off2 2nd-2 | GTGACTGGAGTTCAGACGTGTGCTCTTCCGATCTAAGGCTCCTTGCCTTTACATATAGG |
| Emxl off target 3 | 38 | TA419 EMX-off3 1st-1 | TCACTTTTGTCAATTCATGCCACCATCAGT |
| | 39 | TA420 EMX-off3 1st-2 | GCCACCTCCACTCTGCCAGGAATAGGTTCA |
| | 40 | TA421 EMX-off3 2nd-1 | TCTTTCCCTACACGACGCTCTTCCGATCTATGGACTGTCCTGTGAGCCCGTGGC |
| | 41 | TA422 EMX-off3 2nd-2 | GTGACTGGAGTTCAGACGTGTGCTCTTCCGATCTCTCGGTGGCCTGCAAGTGGAAAGCC |
| Emxl off target 4 | 42 | TA423 EMX-off4 1st-1 | GGGACCACTTGAAGTGAGTAAAATTATAGG |
| | 43 | TA424 EMX-off4 1st-2 | CCCAGCTGTTGCTAGCTTATGGCCAGTCCT |
| | 44 | TA425 EMX-off4 2nd-1 | TCTTTCCCTACACGACGCTCTTCCGATCTCACTGCCTTTCGGGCTAGCCTCCAA |
| | 45 | TA426 EMX-off4 2nd-2 | GTGACTGGAGTTCAGACGTGTGCTCTTCCGATCTTAGATGTTAATAGGTTATTGGGGTG |

Fragments amplified from genomic DNA with a pair of 1st primers were amplified again with a pair of 2nd primers to add an adapter sequence for NGS.

TABLE 3

| target name each editing construct | NGS read number | detected indel (%) in total | target sequence | | | | | | | | | | | | | | |
|---|---|---|---|---|---|---|---|---|---|---|---|---|---|---|---|---|---|
| Emx1 | Read | Indel (%) | −25<br>G | −24<br>G | −23<br>C | −22<br>C | −21<br>T | −20<br>G | −19<br>A | −18<br>G | −17<br>T | −16<br>C | −15<br>C | −14<br>G | −13<br>A | −12<br>G | −11<br>C |
| Cas9 | 143352 | 11.5 | | | | | | | | | | | | | | | |
| nCas9 PmCDA1 | 139289 | 0.15 | | | | | | | | | | T<br>1.49<br>G<br>0.52<br>A<br>0.35 | T<br>0.44<br>G<br>0.32 | | | | T<br>0.38 |
| nCas9 PmCDA1 UGI | 60714 | 0.16 | | | | | | | | | | T<br>7.38<br>G<br>0.31<br>A<br>0.11 | T<br>2.29<br>G<br>0.35 | | | | T<br>1.23<br>G<br>0.14 |
| dCas9 PmCDA1 | 104633 | 0.11 | | | | | | | | | | | | | | | |
| dCas9 PmCDA1 UGI | 119871 | 0.13 | | | | | | | | | | T<br>1.82 | T<br>0.47 | | | | T<br>0.36 |
| Emx1 off target 2 | Read | Indel (%) | −25<br>G | −24<br>A | −23<br>C | −22<br>A | −21<br>A | −20<br>G | −19<br>A | −18<br>G | −17<br>T | −16<br>C | −15<br>T | −14<br>A | −13<br>A | −12<br>G | −11<br>C |
| Cas9 | 33354 | 1.51 | | | | | | | | | | | | | | | |
| nCas9 PmCDA1 | 67209 | 0.49 | | | | | | | | | | T<br>0.19<br>G<br>0.56 | | | | | |
| nCas9 PmCDA1 UGI | 130203 | 0.48 | | | | | | | | | | T<br>0.77 | | | | | |
| dCas9 PmCDA1 | 22108 | 0.5 | | | | | | | | | | | | | | | |
| dCas9 PmCDA1 UGI | 63161 | 0.46 | | | | | | | | | | | | | | | |
| Emx1 off target 3 | Read | Indel (%) | −25<br>A | −24<br>T | −23<br>G | −22<br>A | −21<br>G | −20<br>G | −19<br>A | −18<br>G | −17<br>G | −16<br>C | −15<br>C | −14<br>G | −13<br>A | −12<br>G | −11<br>C |
| Cas9 | 228515 | 2.85 | | | | | | | | | | | | | | | T<br>0.24 |
| nCas9 PmCDA1 | 338152 | 0.76 | | | | | | | | | | T<br>0.2 | | | | T<br>0.18 | T<br>0.25 |
| nCas9 PmCDA1 UGI | 210475 | 0.34 | | | | | | | | | | T<br>0.14 | T<br>0.17 | | | A<br>0.14 | T<br>0.29 |
| dCas9 PmCDA1 | 258150 | 0.29 | | | | | | | | | | | | | | | T<br>0.21 |
| dCas9 PmCDA1 UGI | 187272 | 0.31 | | | | | | | | | | | | | | | T<br>0.21 |
| Emx1 off target 4 | Read | Indel (%) | −25<br>G | −24<br>A | −23<br>C | −22<br>C | −21<br>T | −20<br>G | −19<br>A | −18<br>G | −17<br>T | −16<br>C | −15<br>C | −14<br>T | −13<br>A | −12<br>G | −11<br>C |
| Cas9 | 93074 | 1.02 | | | | | | | | | | | T<br>1.12 | | | | |
| nCas9 PmCDA1 | 48271 | 0 | | | | | | | | | | | T<br>1.25 | | | | |
| nCas9 PmCDA1 UGI | 71071 | 0 | | | | | | | | | | | T<br>1.25 | | | | T<br>0.19 |
| dCas9 PmCDA1 | 69603 | 0 | | | | | | | | | | | T<br>1.13 | | | | |
| dCas9 PmCDA1 UGI | 66474 | 0 | | | | | | | | | | | T<br>1.12 | | | | |

TABLE 3-continued

| target name each editing construct | NGS read number | detected indel (%) in total | | | | | | target sequence | | | | | | PAM | | | | |
|---|---|---|---|---|---|---|---|---|---|---|---|---|---|---|---|---|---|---|
| Emx1 | Read | Indel (%) | −10 A | −9 G | −8 A | −7 A | −6 G | −5 A | −4 A | −3 G | −2 A | −1 A | 0 G | 1 G | 2 G | 3 C | 4 T | 5 C |
| Cas9 | 143352 | 11.5 | | | | | | | | | | | | | | | | |
| nCas9 PmCDA1 | 139289 | 0.15 | | | | | | | | | | | | | | | | |
| nCas9 PmCDA1 UGI | 60714 | 0.16 | | | | | | | | | | | | | | | | |
| dCas9 PmCDA1 | 104633 | 0.11 | | | | | | | | | | | | | | | | |
| dCas9 PmCDA1 UGI | 119871 | 0.13 | | | | | | | | | | | | | | | | |
| Emx1 off target 2 | Read | Indel (%) | −10 A | −9 G | −8 A | −7 A | −6 G | −5 A | −4 A | −3 G | −2 A | −1 A | 0 G | 1 A | 2 G | 3 A | 4 G | 5 C |
| Cas9 | 33354 | 1.51 | | | | | | | | | | | | | | | | T 0.16 |
| nCas9 PmCDA1 | 67209 | 0.49 | | | | | | | | | | G 0.19 | | | | | | T 0.18 |
| nCas9 PmCDA1 UGI | 130203 | 0.48 | | | | | | | | | | | | | | | | T 0.2 |
| dCas9 PmCDA1 | 22108 | 0.5 | | | | | | | | | | | | | | | | T 0.23 |
| dCas9 PmCDA1 UGI | 63161 | 0.46 | | | | | | | | | | | | | | | | T 0.22 |
| Emx1 off target 3 | Read | Indel (%) | −10 A | −9 G | −8 A | −7 A | −6 G | −5 A | −4 A | −3 A | −2 G | −1 A | 0 C | 1 G | 2 G | 3 C | 4 G | 5 A |
| Cas9 | 228515 | 2.85 | | | | | | | | | | | | | | | | |
| nCas9 PmCDA1 | 338152 | 0.76 | | | | | | | | | | | | | | | | |
| nCas9 PmCDA1 UGI | 210475 | 0.34 | | | | | | | | | | | | | | | | |
| dCas9 PmCDA1 | 258150 | 0.29 | | | | | | | | | | | | | | | | |
| dCas9 PmCDA1 UGI | 187272 | 0.31 | | | | | | | | | | | | | | | | |
| Emx1 off target 4 | Read | Indel (%) | −10 A | −9 G | −8 G | −7 A | −6 G | −5 A | −4 A | −3 G | −2 A | −1 A | 0 G | 1 A | 2 G | 3 G | 4 C | 5 A |
| Cas9 | 93074 | 1.02 | | | | | | | | | | | | | | A 0.14 | | |
| nCas9 PmCDA1 | 48271 | 0 | | | | | | | | | | | | | | | | |
| nCas9 PmCDA1 UGI | 71071 | 0 | | | | | | | | | | | | | | | | |
| dCas9 PmCDA1 | 69603 | 0 | | | | | | | | | | | | | | | T 0.17 | |
| dCas9 PmCDA1 UGI | 66474 | 0 | | | | | | | | | | | | | | | T 0.17 | |

From Table 3, a mutation introduction efficiency improving effect by the combined use of UGI was found even when human cells were used. Furthermore, it was suggested that the ratio of off-target mutation rate to on-target can be lowered, namely, the risk of off-target mutation can be suppressed. To be specific, when nCas9-PmCDA1-UGI was used, for example, the ratio of the substitution rate of cytosine at the corresponding position of the off-target candidate to the substitution rate of the −16th cytosine in the target sequence of EMX1 was not more than 1/10. When nCas9-PmCDA1-UGI was used, the mutation rate was improved in the target sequence of EMX1 as compared to that of nCas9-PmCDA1 without combined use of UGI; however, in the off-target candidate sequence, the mutation rate showed almost no difference and off-target mutation was suppressed. Similarly, when dCas9-PmCDA1-UGI was used, the mutation rate was improved in the target sequence of EMX1 as compared to that of dCas9-PmCDA1 without combined use of UGI; however, the mutation rate showed almost no difference in the off-target candidate sequence and off-target mutation was suppressed. As for the −15th cytosine in the off-target candidate sequence 4 (sequence name: Emx1 off target 4) in Table 3, substitution occurred at the same rate irrespective of the vector used. Since substitution is found similarly in Cas9 as well, these substitutions were highly possibly caused by sequencing errors.

INDUSTRIAL APPLICABILITY

The present invention makes it possible to safely introduce site specific mutation into any species highly efficiently without accompanying insertion of a foreign DNA or double-stranded DNA breaks, and is extremely useful.

This application is based on a patent application No. 2016-085631 filed in Japan (filing date: Apr. 21, 2016), the contents of which are incorporated in full herein.

The invention claimed is:

1. A method of modifying a plurality of targeted sites of a double-stranded DNA, comprising a step of introducing a complex comprising a nucleic acid sequence-recognizing module that specifically binds to a target nucleotide sequence in the targeted sites of a double-stranded DNA bonded to *Petromyzon marinus* cytosine deaminase 1 (PmCDA1) or a nucleic acid encoding the complex, into a mammalian cell containing the double-stranded DNA, and culturing the mammalian cell at a temperature of 20° C. to 25° C. at least temporarily to convert one or more nucleotides in the targeted sites to other one or more nucleotides or delete one or more nucleotides, or insert one or more nucleotides into said targeted sites, without cleaving at least one strand of said double-stranded DNA in the targeted sites, wherein the nucleic acid sequence-recognizing module is a clustered regularly interspaced short palindromic repeats (CRISPR)-CRISPR associated (Cas) system comprising a guide RNA complementary to the target nucleotide sequence and a Cas selected from Cas9 and Cpf1, wherein at least one DNA cleavage ability of Cas is inactivated, wherein the PmCDA1 has the amino acid sequence set forth in SEQ ID NO: 2, wherein the PmCDA1 is fused to the nucleic acid sequence-recognizing module by a linker comprising Glycine Serine (GS) linker, wherein the complex further comprises a base excision repair inhibitor that is a uracil DNA glycosylase inhibitor (Ugi) linked to PmCDA1, and wherein the nucleic acid is an expression vector which is not capable of autonomous replication in the mammalian cell.

2. The method according to claim 1, wherein said Cas is deficient in two DNA cleavage abilities.

3. The method according to claim 1, wherein the temperature is 25° C.

4. The method according to claim 1, wherein the double-stranded DNA is contacted with the complex by introducing the nucleic acid encoding the complex into a mammalian cell having the double-stranded DNA.

5. The method according to claim 1, wherein the step of culturing is performed overnight after introduction of the complex.

6. The method according to claim 1, wherein the plurality of targeted sites are in different positions.

7. A method of modifying a targeted site of a double-stranded DNA, comprising a step of contacting a complex wherein a nucleic acid sequence-recognizing module that specifically binds to a target nucleotide sequence in a given double-stranded DNA, a nucleic acid base converting enzyme and a base excision repair inhibitor are bonded, with said double-stranded DNA to convert one or more nucleotides in the targeted site to other one or more nucleotides or delete one or more nucleotides, or insert one or more nucleotides into said targeted site, without cleaving at least one strand of said double-stranded DNA in the targeted site, wherein the nucleic acid sequence-recognizing module is a CRISPR-Cas system wherein at least one DNA cleavage ability of Cas is inactivated, wherein said nucleic acid base converting enzyme is *Petromyzon marinus* cytosine deaminase 1 (PmCDA1);

wherein the PmCDA1 has the amino acid sequence set forth in SEQ ID NO: 2, wherein the PmCDA1 is fused to the nucleic acid sequence-recognizing module by a linker comprising Glycine Serine (GS) linker; and wherein the base excision repair inhibitor is a uracil DNA glycosylase inhibitor (Ugi) linked to the PmCDA1.

8. The method according to claim 7, wherein said Cas is deficient in two DNA cleavage abilities.

9. The method according to claim 7, wherein the double-stranded DNA is contacted with the complex by introducing a nucleic acid encoding the complex into a cell having the double-stranded DNA.

10. The method according to claim 9, wherein said cell is a mammalian cell.

11. A nucleic acid-modifying enzyme complex wherein a nucleic acid sequence-recognizing module that specifically binds to a target nucleotide sequence in a given double-stranded DNA, a nucleic acid base converting enzyme and a base excision repair inhibitor are bonded, which complex converts one or more nucleotides in the targeted site to other one or more nucleotides or deletes one or more nucleotides, or inserts one or more nucleotides into said targeted site, without cleaving at least one strand of said double-stranded DNA in the targeted site, wherein the nucleic acid sequence-recognizing module is a CRISPR-Cas system wherein at least one DNA cleavage ability of Cas is inactivated, wherein said nucleic acid base converting enzyme is *Petromyzon marinus* cytosine deaminase 1 (PmCDA1);

wherein the PmCDA1 has the amino acid sequence set forth in SEQ ID NO: 2, wherein the PmCDA1 is fused to the nucleic acid sequence-recognizing module by a linker comprising Glycine Serine (GS) linker; and wherein the base excision repair inhibitor is a uracil DNA glycosylase inhibitor (Ugi) linked to the PmCDA1.

12. A nucleic acid encoding the nucleic acid-modifying enzyme complex according to claim 11.

* * * * *

```
SEQUENCE LISTING

<160> NUMBER OF SEQ ID NOS: 60

<210> SEQ ID NO 1
<211> LENGTH: 624
<212> TYPE: DNA
<213> ORGANISM: Artificial Sequence
<220> FEATURE:
<223> OTHER INFORMATION: Synthetic Sequence - PmCDA1 CDS optimized for
      human cell expression
<220> FEATURE:
<221> NAME/KEY: CDS
<222> LOCATION: (1)..(624)

<400> SEQUENCE: 1

atg aca gac gcc gag tac gtg cgc att cat gag aaa ctg gat att tac       48
Met Thr Asp Ala Glu Tyr Val Arg Ile His Glu Lys Leu Asp Ile Tyr
1               5                   10                  15

acc ttc aag aag cag ttc ttc aac aac aag aaa tct gtg tca cac cgc       96
Thr Phe Lys Lys Gln Phe Phe Asn Asn Lys Lys Ser Val Ser His Arg
            20                  25                  30

tgc tac gtg ctg ttt gag ttg aag cga agg ggc gaa aga agg gct tgc      144
Cys Tyr Val Leu Phe Glu Leu Lys Arg Arg Gly Glu Arg Arg Ala Cys
        35                  40                  45

ttt tgg ggc tat gcc gtc aac aag ccc caa agt ggc acc gag aga gga      192
Phe Trp Gly Tyr Ala Val Asn Lys Pro Gln Ser Gly Thr Glu Arg Gly
    50                  55                  60

ata cac gct gag ata ttc agt atc cga aag gtg gaa gag tat ctt cgg      240
Ile His Ala Glu Ile Phe Ser Ile Arg Lys Val Glu Glu Tyr Leu Arg
65                  70                  75                  80

gat aat cct ggg cag ttt acg atc aac tgg tat tcc agc tgg agt cct      288
Asp Asn Pro Gly Gln Phe Thr Ile Asn Trp Tyr Ser Ser Trp Ser Pro
                85                  90                  95

tgc gct gat tgt gcc gag aaa att ctg gaa tgg tat aat cag gaa ctt      336
Cys Ala Asp Cys Ala Glu Lys Ile Leu Glu Trp Tyr Asn Gln Glu Leu
            100                 105                 110

cgg gga aac ggg cac aca ttg aaa atc tgg gcc tgc aag ctg tac tac      384
Arg Gly Asn Gly His Thr Leu Lys Ile Trp Ala Cys Lys Leu Tyr Tyr
        115                 120                 125

gag aag aat gcc cgg aac cag ata gga ctc tgg aat ctg agg gac aat      432
Glu Lys Asn Ala Arg Asn Gln Ile Gly Leu Trp Asn Leu Arg Asp Asn
    130                 135                 140

ggt gta ggc ctg aac gtg atg gtt tcc gag cac tat cag tgt tgt cgg      480
Gly Val Gly Leu Asn Val Met Val Ser Glu His Tyr Gln Cys Cys Arg
145                 150                 155                 160

aag att ttc atc caa agc tct cat aac cag ctc aat gaa aac cgc tgg      528
Lys Ile Phe Ile Gln Ser Ser His Asn Gln Leu Asn Glu Asn Arg Trp
                165                 170                 175

ttg gag aaa aca ctg aaa cgt gcg gag aag cgg aga tcc gag ctg agc      576
Leu Glu Lys Thr Leu Lys Arg Ala Glu Lys Arg Arg Ser Glu Leu Ser
            180                 185                 190

atc atg atc cag gtc aag att ctg cat acc act aag tct cca gcc gtt      624
```

-continued

```
Ile Met Ile Gln Val Lys Ile Leu His Thr Thr Lys Ser Pro Ala Val
        195                 200                 205


<210> SEQ ID NO 2
<211> LENGTH: 208
<212> TYPE: PRT
<213> ORGANISM: Artificial Sequence
<220> FEATURE:
<223> OTHER INFORMATION: Synthetic Construct

<400> SEQUENCE: 2

Met Thr Asp Ala Glu Tyr Val Arg Ile His Glu Lys Leu Asp Ile Tyr
1               5                   10                  15

Thr Phe Lys Lys Gln Phe Phe Asn Asn Lys Lys Ser Val Ser His Arg
            20                  25                  30

Cys Tyr Val Leu Phe Glu Leu Lys Arg Arg Gly Glu Arg Arg Ala Cys
        35                  40                  45

Phe Trp Gly Tyr Ala Val Asn Lys Pro Gln Ser Gly Thr Glu Arg Gly
    50                  55                  60

Ile His Ala Glu Ile Phe Ser Ile Arg Lys Val Glu Glu Tyr Leu Arg
65                  70                  75                  80

Asp Asn Pro Gly Gln Phe Thr Ile Asn Trp Tyr Ser Ser Trp Ser Pro
                85                  90                  95

Cys Ala Asp Cys Ala Glu Lys Ile Leu Glu Trp Tyr Asn Gln Glu Leu
            100                 105                 110

Arg Gly Asn Gly His Thr Leu Lys Ile Trp Ala Cys Lys Leu Tyr Tyr
        115                 120                 125

Glu Lys Asn Ala Arg Asn Gln Ile Gly Leu Trp Asn Leu Arg Asp Asn
    130                 135                 140

Gly Val Gly Leu Asn Val Met Val Ser Glu His Tyr Gln Cys Cys Arg
145                 150                 155                 160

Lys Ile Phe Ile Gln Ser Ser His Asn Gln Leu Asn Glu Asn Arg Trp
                165                 170                 175

Leu Glu Lys Thr Leu Lys Arg Ala Glu Lys Arg Arg Ser Glu Leu Ser
            180                 185                 190

Ile Met Ile Gln Val Lys Ile Leu His Thr Thr Lys Ser Pro Ala Val
        195                 200                 205


<210> SEQ ID NO 3
<211> LENGTH: 4116
<212> TYPE: DNA
<213> ORGANISM: Artificial Sequence
<220> FEATURE:
<223> OTHER INFORMATION: Synthetic Sequence - Streptococcus pyogenes-
      derived Cas9 CDS optimized for eucaryotic cell expression
<220> FEATURE:
<221> NAME/KEY: CDS
<222> LOCATION: (1)..(4116)

<400> SEQUENCE: 3

atg gac aag aag tac tcc att ggg ctc gat atc ggc aca aac agc gtc       48
Met Asp Lys Lys Tyr Ser Ile Gly Leu Asp Ile Gly Thr Asn Ser Val
1               5                   10                  15

ggt tgg gcc gtc att acg gac gag tac aag gtg ccg agc aaa aaa ttc       96
Gly Trp Ala Val Ile Thr Asp Glu Tyr Lys Val Pro Ser Lys Lys Phe
            20                  25                  30

aaa gtt ctg ggc aat acc gat cgc cac agc ata aag aag aac ctc att      144
Lys Val Leu Gly Asn Thr Asp Arg His Ser Ile Lys Lys Asn Leu Ile
        35                  40                  45

ggc gcc ctc ctg ttc gac tcc ggg gag acg gcc gaa gcc acg cgg ctc      192
```

-continued

```
Gly Ala Leu Leu Phe Asp Ser Gly Glu Thr Ala Glu Ala Thr Arg Leu
    50                  55                  60

aaa aga aca gca cgg cgc aga tat acc cgc aga aag aat cgg atc tgc      240
Lys Arg Thr Ala Arg Arg Arg Tyr Thr Arg Arg Lys Asn Arg Ile Cys
65                  70                  75                  80

tac ctg cag gag atc ttt agt aat gag atg gct aag gtg gat gac tct      288
Tyr Leu Gln Glu Ile Phe Ser Asn Glu Met Ala Lys Val Asp Asp Ser
                85                  90                  95

ttc ttc cat agg ctg gag gag tcc ttt ttg gtg gag gag gat aaa aag      336
Phe Phe His Arg Leu Glu Glu Ser Phe Leu Val Glu Glu Asp Lys Lys
            100                 105                 110

cac gag cgc cac cca atc ttt ggc aat atc gtg gac gag gtg gcg tac      384
His Glu Arg His Pro Ile Phe Gly Asn Ile Val Asp Glu Val Ala Tyr
        115                 120                 125

cat gaa aag tac cca acc ata tat cat ctg agg aag aag ctt gta gac      432
His Glu Lys Tyr Pro Thr Ile Tyr His Leu Arg Lys Lys Leu Val Asp
    130                 135                 140

agt act gat aag gct gac ttg cgg ttg atc tat ctc gcg ctg gcg cat      480
Ser Thr Asp Lys Ala Asp Leu Arg Leu Ile Tyr Leu Ala Leu Ala His
145                 150                 155                 160

atg atc aaa ttt cgg gga cac ttc ctc atc gag ggg gac ctg aac cca      528
Met Ile Lys Phe Arg Gly His Phe Leu Ile Glu Gly Asp Leu Asn Pro
                165                 170                 175

gac aac agc gat gtc gac aaa ctc ttt atc caa ctg gtt cag act tac      576
Asp Asn Ser Asp Val Asp Lys Leu Phe Ile Gln Leu Val Gln Thr Tyr
            180                 185                 190

aat cag ctt ttc gaa gag aac ccg atc aac gca tcc gga gtt gac gcc      624
Asn Gln Leu Phe Glu Glu Asn Pro Ile Asn Ala Ser Gly Val Asp Ala
        195                 200                 205

aaa gca atc ctg agc gct agg ctg tcc aaa tcc cgg cgg ctc gaa aac      672
Lys Ala Ile Leu Ser Ala Arg Leu Ser Lys Ser Arg Arg Leu Glu Asn
    210                 215                 220

ctc atc gca cag ctc cct ggg gag aag aag aac ggc ctg ttt ggt aat      720
Leu Ile Ala Gln Leu Pro Gly Glu Lys Lys Asn Gly Leu Phe Gly Asn
225                 230                 235                 240

ctt atc gcc ctg tca ctc ggg ctg acc ccc aac ttt aaa tct aac ttc      768
Leu Ile Ala Leu Ser Leu Gly Leu Thr Pro Asn Phe Lys Ser Asn Phe
                245                 250                 255

gac ctg gcc gaa gat gcc aag ctt caa ctg agc aaa gac acc tac gat      816
Asp Leu Ala Glu Asp Ala Lys Leu Gln Leu Ser Lys Asp Thr Tyr Asp
            260                 265                 270

gat gat ctc gac aat ctg ctg gcc cag atc ggc gac cag tac gca gac      864
Asp Asp Leu Asp Asn Leu Leu Ala Gln Ile Gly Asp Gln Tyr Ala Asp
        275                 280                 285

ctt ttt ttg gcg gca aag aac ctg tca gac gcc att ctg ctg agt gat      912
Leu Phe Leu Ala Ala Lys Asn Leu Ser Asp Ala Ile Leu Leu Ser Asp
    290                 295                 300

att ctg cga gtg aac acg gag atc acc aaa gct ccg ctg agc gct agt      960
Ile Leu Arg Val Asn Thr Glu Ile Thr Lys Ala Pro Leu Ser Ala Ser
305                 310                 315                 320

atg atc aag cgc tat gat gag cac cac caa gac ttg act ttg ctg aag     1008
Met Ile Lys Arg Tyr Asp Glu His His Gln Asp Leu Thr Leu Leu Lys
                325                 330                 335

gcc ctt gtc aga cag caa ctg cct gag aag tac aag gaa att ttc ttc     1056
Ala Leu Val Arg Gln Gln Leu Pro Glu Lys Tyr Lys Glu Ile Phe Phe
            340                 345                 350

gat cag tct aaa aat ggc tac gcc gga tac att gac ggc gga gca agc     1104
Asp Gln Ser Lys Asn Gly Tyr Ala Gly Tyr Ile Asp Gly Gly Ala Ser
        355                 360                 365
```

-continued

```
cag gag gaa ttt tac aaa ttt att aag ccc atc ttg gaa aaa atg gac      1152
Gln Glu Glu Phe Tyr Lys Phe Ile Lys Pro Ile Leu Glu Lys Met Asp
    370                 375                 380

ggc acc gag gag ctg ctg gta aag ctt aac aga gaa gat ctg ttg cgc      1200
Gly Thr Glu Glu Leu Leu Val Lys Leu Asn Arg Glu Asp Leu Leu Arg
385                 390                 395                 400

aaa cag cgc act ttc gac aat gga agc atc ccc cac cag att cac ctg      1248
Lys Gln Arg Thr Phe Asp Asn Gly Ser Ile Pro His Gln Ile His Leu
                405                 410                 415

ggc gaa ctg cac gct atc ctc agg cgg caa gag gat ttc tac ccc ttt      1296
Gly Glu Leu His Ala Ile Leu Arg Arg Gln Glu Asp Phe Tyr Pro Phe
            420                 425                 430

ttg aaa gat aac agg gaa aag att gag aaa atc ctc aca ttt cgg ata      1344
Leu Lys Asp Asn Arg Glu Lys Ile Glu Lys Ile Leu Thr Phe Arg Ile
        435                 440                 445

ccc tac tat gta ggc ccc ctc gcc cgg gga aat tcc aga ttc gcg tgg      1392
Pro Tyr Tyr Val Gly Pro Leu Ala Arg Gly Asn Ser Arg Phe Ala Trp
    450                 455                 460

atg act cgc aaa tca gaa gag acc atc act ccc tgg aac ttc gag gaa      1440
Met Thr Arg Lys Ser Glu Glu Thr Ile Thr Pro Trp Asn Phe Glu Glu
465                 470                 475                 480

gtc gtg gat aag ggg gcc tct gcc cag tcc ttc atc gaa agg atg act      1488
Val Val Asp Lys Gly Ala Ser Ala Gln Ser Phe Ile Glu Arg Met Thr
                485                 490                 495

aac ttt gat aaa aat ctg cct aac gaa aag gtg ctt cct aaa cac tct      1536
Asn Phe Asp Lys Asn Leu Pro Asn Glu Lys Val Leu Pro Lys His Ser
            500                 505                 510

ctg ctg tac gag tac ttc aca gtt tat aac gag ctc acc aag gtc aaa      1584
Leu Leu Tyr Glu Tyr Phe Thr Val Tyr Asn Glu Leu Thr Lys Val Lys
        515                 520                 525

tac gtc aca gaa ggg atg aga aag cca gca ttc ctg tct gga gag cag      1632
Tyr Val Thr Glu Gly Met Arg Lys Pro Ala Phe Leu Ser Gly Glu Gln
    530                 535                 540

aag aaa gct atc gtg gac ctc ctc ttc aag acg aac cgg aaa gtt acc      1680
Lys Lys Ala Ile Val Asp Leu Leu Phe Lys Thr Asn Arg Lys Val Thr
545                 550                 555                 560

gtg aaa cag ctc aaa gaa gac tat ttc aaa aag att gaa tgt ttc gac      1728
Val Lys Gln Leu Lys Glu Asp Tyr Phe Lys Lys Ile Glu Cys Phe Asp
                565                 570                 575

tct gtt gaa atc agc gga gtg gag gat cgc ttc aac gca tcc ctg gga      1776
Ser Val Glu Ile Ser Gly Val Glu Asp Arg Phe Asn Ala Ser Leu Gly
            580                 585                 590

acg tat cac gat ctc ctg aaa atc att aaa gac aag gac ttc ctg gac      1824
Thr Tyr His Asp Leu Leu Lys Ile Ile Lys Asp Lys Asp Phe Leu Asp
        595                 600                 605

aat gag gag aac gag gac att ctt gag gac att gtc ctc acc ctt acg      1872
Asn Glu Glu Asn Glu Asp Ile Leu Glu Asp Ile Val Leu Thr Leu Thr
    610                 615                 620

ttg ttt gaa gat agg gag atg att gaa gaa cgc ttg aaa act tac gct      1920
Leu Phe Glu Asp Arg Glu Met Ile Glu Glu Arg Leu Lys Thr Tyr Ala
625                 630                 635                 640

cat ctc ttc gac gac aaa gtc atg aaa cag ctc aag agg cgc cga tat      1968
His Leu Phe Asp Asp Lys Val Met Lys Gln Leu Lys Arg Arg Arg Tyr
                645                 650                 655

aca gga tgg ggg cgg ctg tca aga aaa ctg atc aat ggg atc cga gac      2016
Thr Gly Trp Gly Arg Leu Ser Arg Lys Leu Ile Asn Gly Ile Arg Asp
            660                 665                 670

aag cag agt gga aag aca atc ctg gat ttt ctt aag tcc gat gga ttt      2064
Lys Gln Ser Gly Lys Thr Ile Leu Asp Phe Leu Lys Ser Asp Gly Phe
        675                 680                 685
```

```
gcc aac cgg aac ttc atg cag ttg atc cat gat gac tct ctc acc ttt     2112
Ala Asn Arg Asn Phe Met Gln Leu Ile His Asp Asp Ser Leu Thr Phe
    690                 695                 700

aag gag gac atc cag aaa gca caa gtt tct ggc cag ggg gac agt ctt     2160
Lys Glu Asp Ile Gln Lys Ala Gln Val Ser Gly Gln Gly Asp Ser Leu
705                 710                 715                 720

cac gag cac atc gct aat ctt gca ggt agc cca gct atc aaa aag gga     2208
His Glu His Ile Ala Asn Leu Ala Gly Ser Pro Ala Ile Lys Lys Gly
                725                 730                 735

ata ctg cag acc gtt aag gtc gtg gat gaa ctc gtc aaa gta atg gga     2256
Ile Leu Gln Thr Val Lys Val Val Asp Glu Leu Val Lys Val Met Gly
            740                 745                 750

agg cat aag ccc gag aat atc gtt atc gag atg gcc cga gag aac caa     2304
Arg His Lys Pro Glu Asn Ile Val Ile Glu Met Ala Arg Glu Asn Gln
        755                 760                 765

act acc cag aag gga cag aag aac agt agg gaa agg atg aag agg att     2352
Thr Thr Gln Lys Gly Gln Lys Asn Ser Arg Glu Arg Met Lys Arg Ile
    770                 775                 780

gaa gag ggt ata aaa gaa ctg ggg tcc caa atc ctt aag gaa cac cca     2400
Glu Glu Gly Ile Lys Glu Leu Gly Ser Gln Ile Leu Lys Glu His Pro
785                 790                 795                 800

gtt gaa aac acc cag ctt cag aat gag aag ctc tac ctg tac tac ctg     2448
Val Glu Asn Thr Gln Leu Gln Asn Glu Lys Leu Tyr Leu Tyr Tyr Leu
                805                 810                 815

cag aac ggc agg gac atg tac gtg gat cag gaa ctg gac atc aat cgg     2496
Gln Asn Gly Arg Asp Met Tyr Val Asp Gln Glu Leu Asp Ile Asn Arg
            820                 825                 830

ctc tcc gac tac gac gtg gat cat atc gtg ccc cag tct ttt ctc aaa     2544
Leu Ser Asp Tyr Asp Val Asp His Ile Val Pro Gln Ser Phe Leu Lys
        835                 840                 845

gat gat tct att gat aat aaa gtg ttg aca aga tcc gat aaa aat aga     2592
Asp Asp Ser Ile Asp Asn Lys Val Leu Thr Arg Ser Asp Lys Asn Arg
    850                 855                 860

ggg aag agt gat aac gtc ccc tca gaa gaa gtt gtc aag aaa atg aaa     2640
Gly Lys Ser Asp Asn Val Pro Ser Glu Glu Val Val Lys Lys Met Lys
865                 870                 875                 880

aat tat tgg cgg cag ctg ctg aac gcc aaa ctg atc aca caa cgg aag     2688
Asn Tyr Trp Arg Gln Leu Leu Asn Ala Lys Leu Ile Thr Gln Arg Lys
                885                 890                 895

ttc gat aat ctg act aag gct gaa cga ggt ggc ctg tct gag ttg gat     2736
Phe Asp Asn Leu Thr Lys Ala Glu Arg Gly Gly Leu Ser Glu Leu Asp
            900                 905                 910

aaa gcc ggc ttc atc aaa agg cag ctt gtt gag aca cgc cag atc acc     2784
Lys Ala Gly Phe Ile Lys Arg Gln Leu Val Glu Thr Arg Gln Ile Thr
        915                 920                 925

aag cac gtg gcc caa att ctc gat tca cgc atg aac acc aag tac gat     2832
Lys His Val Ala Gln Ile Leu Asp Ser Arg Met Asn Thr Lys Tyr Asp
    930                 935                 940

gaa aat gac aaa ctg att cga gag gtg aaa gtt att act ctg aag tct     2880
Glu Asn Asp Lys Leu Ile Arg Glu Val Lys Val Ile Thr Leu Lys Ser
945                 950                 955                 960

aag ctg gtc tca gat ttc aga aag gac ttt cag ttt tat aag gtg aga     2928
Lys Leu Val Ser Asp Phe Arg Lys Asp Phe Gln Phe Tyr Lys Val Arg
                965                 970                 975

gag atc aac aat tac cac cat gcg cat gat gcc tac ctg aat gca gtg     2976
Glu Ile Asn Asn Tyr His His Ala His Asp Ala Tyr Leu Asn Ala Val
            980                 985                 990

gta ggc act gca ctt atc aaa aaa  tat ccc aag ctt gaa  tct gaa ttt   3024
Val Gly Thr Ala Leu Ile Lys Lys  Tyr Pro Lys Leu Glu  Ser Glu Phe
```

-continued

```
        995                 1000                1005

gtt tac  gga gac tat aaa gtg  tac gat gtt agg aaa  atg atc gca      3069
Val Tyr  Gly Asp Tyr Lys Val  Tyr Asp Val Arg Lys  Met Ile Ala
    1010                 1015                 1020

aag tct  gag cag gaa ata ggc  aag gcc acc gct aag  tac ttc ttt      3114
Lys Ser  Glu Gln Glu Ile Gly  Lys Ala Thr Ala Lys  Tyr Phe Phe
    1025                 1030                 1035

tac agc  aat att atg aat ttt  ttc aag acc gag att  aca ctg gcc      3159
Tyr Ser  Asn Ile Met Asn Phe  Phe Lys Thr Glu Ile  Thr Leu Ala
    1040                 1045                 1050

aat gga  gag att cgg aag cga  cca ctt atc gaa aca  aac gga gaa      3204
Asn Gly  Glu Ile Arg Lys Arg  Pro Leu Ile Glu Thr  Asn Gly Glu
    1055                 1060                 1065

aca gga  gaa atc gtg tgg gac  aag ggt agg gat ttc  gcg aca gtc      3249
Thr Gly  Glu Ile Val Trp Asp  Lys Gly Arg Asp Phe  Ala Thr Val
    1070                 1075                 1080

cgg aag  gtc ctg tcc atg ccg  cag gtg aac atc gtt  aaa aag acc      3294
Arg Lys  Val Leu Ser Met Pro  Gln Val Asn Ile Val  Lys Lys Thr
    1085                 1090                 1095

gaa gta  cag acc gga ggc ttc  tcc aag gaa agt atc  ctc ccg aaa      3339
Glu Val  Gln Thr Gly Gly Phe  Ser Lys Glu Ser Ile  Leu Pro Lys
    1100                 1105                 1110

agg aac  agc gac aag ctg atc  gca cgc aaa aaa gat  tgg gac ccc      3384
Arg Asn  Ser Asp Lys Leu Ile  Ala Arg Lys Lys Asp  Trp Asp Pro
    1115                 1120                 1125

aag aaa  tac ggc gga ttc gat  tct cct aca gtc gct  tac agt gta      3429
Lys Lys  Tyr Gly Gly Phe Asp  Ser Pro Thr Val Ala  Tyr Ser Val
    1130                 1135                 1140

ctg gtt  gtg gcc aaa gtg gag  aaa ggg aag tct aaa  aaa ctc aaa      3474
Leu Val  Val Ala Lys Val Glu  Lys Gly Lys Ser Lys  Lys Leu Lys
    1145                 1150                 1155

agc gtc  aag gaa ctg ctg ggc  atc aca atc atg gag  cga tca agc      3519
Ser Val  Lys Glu Leu Leu Gly  Ile Thr Ile Met Glu  Arg Ser Ser
    1160                 1165                 1170

ttc gaa  aaa aac ccc atc gac  ttt ctc gag gcg aaa  gga tat aaa      3564
Phe Glu  Lys Asn Pro Ile Asp  Phe Leu Glu Ala Lys  Gly Tyr Lys
    1175                 1180                 1185

gag gtc  aaa aaa gac ctc atc  att aag ctt ccc aag  tac tct ctc      3609
Glu Val  Lys Lys Asp Leu Ile  Ile Lys Leu Pro Lys  Tyr Ser Leu
    1190                 1195                 1200

ttt gag  ctt gaa aac ggc cgg  aaa cga atg ctc gct  agt gcg ggc      3654
Phe Glu  Leu Glu Asn Gly Arg  Lys Arg Met Leu Ala  Ser Ala Gly
    1205                 1210                 1215

gag ctg  cag aaa ggt aac gag  ctg gca ctg ccc tct  aaa tac gtt      3699
Glu Leu  Gln Lys Gly Asn Glu  Leu Ala Leu Pro Ser  Lys Tyr Val
    1220                 1225                 1230

aat ttc  ttg tat ctg gcc agc  cac tat gaa aag ctc  aaa ggg tct      3744
Asn Phe  Leu Tyr Leu Ala Ser  His Tyr Glu Lys Leu  Lys Gly Ser
    1235                 1240                 1245

ccc gaa  gat aat gag cag aag  cag ctg ttc gtg gaa  caa cac aaa      3789
Pro Glu  Asp Asn Glu Gln Lys  Gln Leu Phe Val Glu  Gln His Lys
    1250                 1255                 1260

cac tac  ctt gat gag atc atc  gag caa ata agc gaa  ttc tcc aaa      3834
His Tyr  Leu Asp Glu Ile Ile  Glu Gln Ile Ser Glu  Phe Ser Lys
    1265                 1270                 1275

aga gtg  atc ctc gcc gac gct  aac ctc gat aag gtg  ctt tct gct      3879
Arg Val  Ile Leu Ala Asp Ala  Asn Leu Asp Lys Val  Leu Ser Ala
    1280                 1285                 1290

tac aat  aag cac agg gat aag  ccc atc agg gag cag  gca gaa aac      3924
```

```
Tyr Asn  Lys His Arg Asp Lys  Pro Ile Arg Glu Gln  Ala Glu Asn
    1295                 1300                 1305

att atc  cac ttg ttt act ctg  acc aac ttg ggc gcg  cct gca gcc      3969
Ile Ile  His Leu Phe Thr Leu  Thr Asn Leu Gly Ala  Pro Ala Ala
    1310                 1315                 1320

ttc aag  tac ttc gac acc acc  ata gac aga aag cgg  tac acc tct      4014
Phe Lys  Tyr Phe Asp Thr Thr  Ile Asp Arg Lys Arg  Tyr Thr Ser
    1325                 1330                 1335

aca aag  gag gtc ctg gac gcc  aca ctg att cat cag  tca att acg      4059
Thr Lys  Glu Val Leu Asp Ala  Thr Leu Ile His Gln  Ser Ile Thr
    1340                 1345                 1350

ggg ctc  tat gaa aca aga atc  gac ctc tct cag ctc  ggt gga gac      4104
Gly Leu  Tyr Glu Thr Arg Ile  Asp Leu Ser Gln Leu  Gly Gly Asp
    1355                 1360                 1365

agc agg  gct gac                                                    4116
Ser Arg  Ala Asp
    1370


<210> SEQ ID NO 4
<211> LENGTH: 1372
<212> TYPE: PRT
<213> ORGANISM: Artificial Sequence
<220> FEATURE:
<223> OTHER INFORMATION: Synthetic Construct

<400> SEQUENCE: 4

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
```

-continued

```
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670
```

-continued

```
Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080
```

-continued

```
Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365

Ser Arg  Ala Asp
    1370
```

<210> SEQ ID NO 5
<211> LENGTH: 252
<212> TYPE: DNA
<213> ORGANISM: Artificial Sequence
<220> FEATURE:
<223> OTHER INFORMATION: Synthetic Sequence - PBS2-derived Ugi CDS optimized for eucaryotic cell expression
<220> FEATURE:
<221> NAME/KEY: CDS
<222> LOCATION: (1)..(252)

<400> SEQUENCE: 5

```
atg acc aac ctt tcc gac atc ata gag aag gaa aca ggc aaa cag ttg       48
Met Thr Asn Leu Ser Asp Ile Ile Glu Lys Glu Thr Gly Lys Gln Leu
1               5                   10                  15

gtc atc caa gag tcg ata ctc atg ctt cct gaa gaa gtt gag gag gtc       96
```

-continued

```
Val Ile Gln Glu Ser Ile Leu Met Leu Pro Glu Glu Val Glu Glu Val
            20                  25                  30

att ggg aat aag ccg gaa agt gac att ctc gta cac act gcg tat gat      144
Ile Gly Asn Lys Pro Glu Ser Asp Ile Leu Val His Thr Ala Tyr Asp
        35                  40                  45

gag agc acc gat gag aac gtg atg ctg ctc acg tca gat gcc cca gag      192
Glu Ser Thr Asp Glu Asn Val Met Leu Leu Thr Ser Asp Ala Pro Glu
    50                  55                  60

tac aaa ccc tgg gct ctg gtg att cag gac tct aat gga gag aac aag      240
Tyr Lys Pro Trp Ala Leu Val Ile Gln Asp Ser Asn Gly Glu Asn Lys
65                  70                  75                  80

atc aag atg cta                                                      252
Ile Lys Met Leu


<210> SEQ ID NO 6
<211> LENGTH: 84
<212> TYPE: PRT
<213> ORGANISM: Artificial Sequence
<220> FEATURE:
<223> OTHER INFORMATION: Synthetic Construct

<400> SEQUENCE: 6

Met Thr Asn Leu Ser Asp Ile Ile Glu Lys Glu Thr Gly Lys Gln Leu
1               5                   10                  15

Val Ile Gln Glu Ser Ile Leu Met Leu Pro Glu Glu Val Glu Glu Val
            20                  25                  30

Ile Gly Asn Lys Pro Glu Ser Asp Ile Leu Val His Thr Ala Tyr Asp
        35                  40                  45

Glu Ser Thr Asp Glu Asn Val Met Leu Leu Thr Ser Asp Ala Pro Glu
    50                  55                  60

Tyr Lys Pro Trp Ala Leu Val Ile Gln Asp Ser Asn Gly Glu Asn Lys
65                  70                  75                  80

Ile Lys Met Leu


<210> SEQ ID NO 7
<211> LENGTH: 20
<212> TYPE: DNA
<213> ORGANISM: Cricetulus griseus

<400> SEQUENCE: 7

ccgagatgtc atgaaagaga                                                 20


<210> SEQ ID NO 8
<211> LENGTH: 20
<212> TYPE: DNA
<213> ORGANISM: Cricetulus griseus

<400> SEQUENCE: 8

ccatgacgga atcggtcggc                                                 20


<210> SEQ ID NO 9
<211> LENGTH: 83
<212> TYPE: DNA
<213> ORGANISM: Streptococcus pyogenes

<400> SEQUENCE: 9

gttttagagc tagaaatagc aagttaaaat aaggctagtc cgttatcaac ttgaaaaagt     60

ggcaccgagt cggtggtgct ttt                                             83


<210> SEQ ID NO 10
```

<211> LENGTH: 229
<212> TYPE: DNA
<213> ORGANISM: Homo sapiens

<400> SEQUENCE: 10
aattcgaacg ctgacgtcat caacccgctc caaggaatcg cgggcccagt gtcactaggc 60
gggaacaccc agcgcgcgtg cgccctggca ggaagatggc tgtgagggac aggggagtgg 120
cgccctgcaa tatttgcatg tcgctatgtg ttctgggaaa tcaccataaa cgtgaaatgt 180
ctttggattt gggaatctta taagttctgt atgaggacca cagatcccc 229

<210> SEQ ID NO 11
<211> LENGTH: 21
<212> TYPE: DNA
<213> ORGANISM: Artificial Sequence
<220> FEATURE:
<223> OTHER INFORMATION: Synthetic Sequence - Nuclear transition signal
<220> FEATURE:
<221> NAME/KEY: CDS
<222> LOCATION: (1)..(21)

<400> SEQUENCE: 11 ccc aag aag aag agg aag gtg 21
Pro Lys Lys Lys Arg Lys Val
1 5

<210> SEQ ID NO 12
<211> LENGTH: 7
<212> TYPE: PRT
<213> ORGANISM: Artificial Sequence
<220> FEATURE:
<223> OTHER INFORMATION: Synthetic Sequence - Synthetic Construct

<400> SEQUENCE: 12

Pro Lys Lys Lys Arg Lys Val
1 5

<210> SEQ ID NO 13
<211> LENGTH: 54
<212> TYPE: DNA
<213> ORGANISM: Artificial Sequence
<220> FEATURE:
<223> OTHER INFORMATION: Synthetic Sequence - 2A peptide
<220> FEATURE:
<221> NAME/KEY: CDS
<222> LOCATION: (1)..(54)

<400> SEQUENCE: 13 gaa ggc agg gga agc ctt ctg act tgt ggg gat gtg gaa gaa aac cct 48
Glu Gly Arg Gly Ser Leu Leu Thr Cys Gly Asp Val Glu Glu Asn Pro
1 5 10 15 ggt cca 54
Gly Pro

<210> SEQ ID NO 14
<211> LENGTH: 18
<212> TYPE: PRT
<213> ORGANISM: Artificial Sequence
<220> FEATURE:
<223> OTHER INFORMATION: Synthetic Construct

<400> SEQUENCE: 14

Glu Gly Arg Gly Ser Leu Leu Thr Cys Gly Asp Val Glu Glu Asn Pro
1 5 10 15

Gly Pro

<210> SEQ ID NO 15
<211> LENGTH: 15
<212> TYPE: DNA
<213> ORGANISM: Artificial Sequence
<220> FEATURE:
<223> OTHER INFORMATION: Synthetic Sequence - GS linker
<220> FEATURE:
<221> NAME/KEY: CDS
<222> LOCATION: (1)..(15)

<400> SEQUENCE: 15 ggt gga gga ggt tct 15
Gly Gly Gly Gly Ser
1 5

<210> SEQ ID NO 16
<211> LENGTH: 5
<212> TYPE: PRT
<213> ORGANISM: Artificial Sequence
<220> FEATURE:
<223> OTHER INFORMATION: Synthetic Construct

<400> SEQUENCE: 16

Gly Gly Gly Gly Ser
1 5

<210> SEQ ID NO 17
<211> LENGTH: 122
<212> TYPE: DNA
<213> ORGANISM: Artificial Sequence
<220> FEATURE:
<223> OTHER INFORMATION: Synthetic Sequence - SV40 poly A signal terminator

<400> SEQUENCE: 17
aacttgttta ttgcagctta taatggttac aaataaagca atagcatcac aaatttcaca 60
aataaagcat ttttttcact gcattctagt tgtggtttgt ccaaactcat caatgtatct 120
ta 122

<210> SEQ ID NO 18
<211> LENGTH: 25
<212> TYPE: DNA
<213> ORGANISM: Artificial Sequence
<220> FEATURE:
<223> OTHER INFORMATION: Synthetic Sequence - PCR forward primer

<400> SEQUENCE: 18
ggctacatag agggatcctg tgtca 25

<210> SEQ ID NO 19
<211> LENGTH: 25
<212> TYPE: DNA
<213> ORGANISM: Artificial Sequence
<220> FEATURE:
<223> OTHER INFORMATION: Synthetic Sequence - PCR reverse primer

<400> SEQUENCE: 19
acagtagctc ttcagtctga taaaa 25

<210> SEQ ID NO 20
<211> LENGTH: 19
<212> TYPE: RNA
<213> ORGANISM: Francisella novicida
<220> FEATURE:
<221> NAME/KEY: misc_structure
<222> LOCATION: (1)..(19)

<223> OTHER INFORMATION: crRNA direct repeat sequence.

<400> SEQUENCE: 20
aauuucuacu guuguagau 19

<210> SEQ ID NO 21
<211> LENGTH: 20
<212> TYPE: DNA
<213> ORGANISM: Homo sapiens

<400> SEQUENCE: 21
gagtccgagc agaagaagaa 20

<210> SEQ ID NO 22
<211> LENGTH: 20
<212> TYPE: DNA
<213> ORGANISM: Homo sapiens

<400> SEQUENCE: 22
gagttagagc agaagaagaa 20

<210> SEQ ID NO 23
<211> LENGTH: 20
<212> TYPE: DNA
<213> ORGANISM: Homo sapiens

<400> SEQUENCE: 23
gagtctaagc agaagaagaa 20

<210> SEQ ID NO 24
<211> LENGTH: 20
<212> TYPE: DNA
<213> ORGANISM: Homo sapiens

<400> SEQUENCE: 24
gaggccgagc agaagaaaga 20

<210> SEQ ID NO 25
<211> LENGTH: 20
<212> TYPE: DNA
<213> ORGANISM: Homo sapiens

<400> SEQUENCE: 25
gagtcctagc aggagaagaa 20

<210> SEQ ID NO 26
<211> LENGTH: 35
<212> TYPE: DNA
<213> ORGANISM: Artificial Sequence
<220> FEATURE:
<223> OTHER INFORMATION: Synthetic Sequence - PCR primer (EMX 1st primer)

<400> SEQUENCE: 26
gtagtctggc tgtcacaggc catactcttc cacat 35

<210> SEQ ID NO 27
<211> LENGTH: 35
<212> TYPE: DNA
<213> ORGANISM: Artificial Sequence
<220> FEATURE:
<223> OTHER INFORMATION: Synthetic Sequence - PCR primer (EMX 1st primer)

<400> SEQUENCE: 27
gtgggtgacc cacccaagca gcaggctctc cacca 35

<210> SEQ ID NO 28
<211> LENGTH: 59
<212> TYPE: DNA
<213> ORGANISM: Artificial Sequence
<220> FEATURE:
<223> OTHER INFORMATION: Synthetic Sequence - PCR primer (EMX 2nd primer)

<400> SEQUENCE: 28
tctttcccta cacgacgctc ttccgatcta cttagctgga gtgtggaggc tatcttggc 59

<210> SEQ ID NO 29
<211> LENGTH: 59
<212> TYPE: DNA
<213> ORGANISM: Artificial Sequence
<220> FEATURE:
<223> OTHER INFORMATION: Synthetic Sequence - PCR primer (EMX 2nd primer)

<400> SEQUENCE: 29
gtgactggag ttcagacgtg tgctcttccg atctggctag ggactggcca gagtccagc 59

<210> SEQ ID NO 30
<211> LENGTH: 35
<212> TYPE: DNA
<213> ORGANISM: Artificial Sequence
<220> FEATURE:
<223> OTHER INFORMATION: Synthetic Sequence - PCR primer (EMX-off1 1st primer)

<400> SEQUENCE: 30
ctgcccatat ccaccacaag caagttagtc atcaa 35

<210> SEQ ID NO 31
<211> LENGTH: 30
<212> TYPE: DNA
<213> ORGANISM: Artificial Sequence
<220> FEATURE:
<223> OTHER INFORMATION: Synthetic Sequence - PCR primer (EMX-off1 1st primer)

<400> SEQUENCE: 31
aatcaaaatc tctatgtgtg gggcacaggg 30

<210> SEQ ID NO 32
<211> LENGTH: 54
<212> TYPE: DNA
<213> ORGANISM: Artificial Sequence
<220> FEATURE:
<223> OTHER INFORMATION: Synthetic Sequence - PCR primer (EMX-off1 2nd primer)

<400> SEQUENCE: 32
tctttcccta cacgacgctc ttccgatctc attggctaga attcagactt caag 54

<210> SEQ ID NO 33
<211> LENGTH: 59
<212> TYPE: DNA
<213> ORGANISM: Artificial Sequence
<220> FEATURE:
<223> OTHER INFORMATION: Synthetic Sequence - PCR primer (EMX-off1 2nd primer)

<400> SEQUENCE: 33

-continued gtgactggag ttcagacgtg tgctcttccg atctatgagg gagatgtact ctcaagtga 59

<210> SEQ ID NO 34
<211> LENGTH: 35
<212> TYPE: DNA
<213> ORGANISM: Artificial Sequence
<220> FEATURE:
<223> OTHER INFORMATION: Synthetic Sequence - PCR primer (EMX-off2 1st primer)

<400> SEQUENCE: 34
catgttccct caccettggc atctacacac tttct 35

<210> SEQ ID NO 35
<211> LENGTH: 30
<212> TYPE: DNA
<213> ORGANISM: Artificial Sequence
<220> FEATURE:
<223> OTHER INFORMATION: Synthetic Sequence - PCR primer (EMX-off2 1st primer)

<400> SEQUENCE: 35
tagtttaccc tgaggcaata tctgactcca 30

<210> SEQ ID NO 36
<211> LENGTH: 54
<212> TYPE: DNA
<213> ORGANISM: Artificial Sequence
<220> FEATURE:
<223> OTHER INFORMATION: Synthetic Sequence - PCR primer (EMX-off2 2nd primer)

<400> SEQUENCE: 36
tctttcccta cacgacgctc ttccgatctt cattttcaaa tgcctattga gcgg 54

<210> SEQ ID NO 37
<211> LENGTH: 59
<212> TYPE: DNA
<213> ORGANISM: Artificial Sequence
<220> FEATURE:
<223> OTHER INFORMATION: Synthetic Sequence - PCR primer (EMX-off2 2nd primer)

<400> SEQUENCE: 37
gtgactggag ttcagacgtg tgctcttccg atctaaggct ccttgccttt acatatagg 59

<210> SEQ ID NO 38
<211> LENGTH: 30
<212> TYPE: DNA
<213> ORGANISM: Artificial Sequence
<220> FEATURE:
<223> OTHER INFORMATION: Synthetic Sequence - PCR primer (EMX-off3 1st primer)

<400> SEQUENCE: 38
tcacttttgt caattcatgc caccatcagt 30

<210> SEQ ID NO 39
<211> LENGTH: 30
<212> TYPE: DNA
<213> ORGANISM: Artificial Sequence
<220> FEATURE:
<223> OTHER INFORMATION: Synthetic Sequence - PCR primer (EMX-off3 1st primer)

<400> SEQUENCE: 39
gccacctcca ctctgccagg aataggttca 30

<210> SEQ ID NO 40
<211> LENGTH: 54
<212> TYPE: DNA
<213> ORGANISM: Artificial Sequence
<220> FEATURE:
<223> OTHER INFORMATION: Synthetic Sequence - PCR primer (EMX-off3 2nd primer)

<400> SEQUENCE: 40
tctttcccta cacgacgctc ttccgatcta tggactgtcc tgtgagcccg tggc 54

<210> SEQ ID NO 41
<211> LENGTH: 59
<212> TYPE: DNA
<213> ORGANISM: Artificial Sequence
<220> FEATURE:
<223> OTHER INFORMATION: Synthetic Sequence - PCR primer (EMX-off3 2nd primer)

<400> SEQUENCE: 41
gtgactggag ttcagacgtg tgctcttccg atctctcggt ggcctgcaag tggaaagcc 59

<210> SEQ ID NO 42
<211> LENGTH: 30
<212> TYPE: DNA
<213> ORGANISM: Artificial Sequence
<220> FEATURE:
<223> OTHER INFORMATION: Synthetic Sequence - PCR primer (EMX-off4 1st primer)

<400> SEQUENCE: 42
gggaccactt gaagtgagta aaattatagg 30

<210> SEQ ID NO 43
<211> LENGTH: 30
<212> TYPE: DNA
<213> ORGANISM: Artificial Sequence
<220> FEATURE:
<223> OTHER INFORMATION: Synthetic Sequence - PCR primer (EMX-off4 1st primer)

<400> SEQUENCE: 43
cccagctgtt gctagcttat ggccagtcct 30

<210> SEQ ID NO 44
<211> LENGTH: 54
<212> TYPE: DNA
<213> ORGANISM: Artificial Sequence
<220> FEATURE:
<223> OTHER INFORMATION: Synthetic Sequence - PCR primer (EMX-off4 2nd primer)

<400> SEQUENCE: 44
tctttcccta cacgacgctc ttccgatctc actgcctttc gggctagcct ccaa 54

<210> SEQ ID NO 45
<211> LENGTH: 59
<212> TYPE: DNA
<213> ORGANISM: Artificial Sequence
<220> FEATURE:
<223> OTHER INFORMATION: Synthetic Sequence - PCR primer (EMX-off4 2nd primer)

<400> SEQUENCE: 45
gtgactggag ttcagacgtg tgctcttccg atcttagatg ttaataggtt attggggtg 59

-continued

<210> SEQ ID NO 46
<211> LENGTH: 18
<212> TYPE: PRT
<213> ORGANISM: Cricetulus griseus

<400> SEQUENCE: 46

Thr Glu Arg Leu Ala Arg Asp Val Met Lys Glu Met Gly Gly His His
1 5 10 15

Ile Val

<210> SEQ ID NO 47
<211> LENGTH: 55
<212> TYPE: DNA
<213> ORGANISM: Cricetulus griseus

<400> SEQUENCE: 47
gactgaaaga cttgcccgag atgtcatgaa agagatggga ggccatcaca ttgtg 55

<210> SEQ ID NO 48
<211> LENGTH: 29
<212> TYPE: DNA
<213> ORGANISM: Cricetulus griseus

<400> SEQUENCE: 48
gactgaaaga cttgcccgag atgtcatga 29

<210> SEQ ID NO 49
<211> LENGTH: 53
<212> TYPE: DNA
<213> ORGANISM: Cricetulus griseus

<400> SEQUENCE: 49
gactgaaaga cttgcccgag atgtcatgaa agatgggagg ccatcacatt gtg 53

<210> SEQ ID NO 50
<211> LENGTH: 55
<212> TYPE: DNA
<213> ORGANISM: Cricetulus griseus

<400> SEQUENCE: 50
gactgaaaga cttgcccgag atgtcatgaa agagatggga ggccatcaca ttgtg 55

<210> SEQ ID NO 51
<211> LENGTH: 56
<212> TYPE: DNA
<213> ORGANISM: Cricetulus griseus

<400> SEQUENCE: 51
gactgaaaga cttgcccgag atgtcatgaa agaggatggg aggccatcac attgtg 56

<210> SEQ ID NO 52
<211> LENGTH: 45
<212> TYPE: DNA
<213> ORGANISM: Cricetulus griseus

<400> SEQUENCE: 52
gactgaaaga cttgcctgaa agagatggga ggccatcaca ttgtg 45

<210> SEQ ID NO 53
<211> LENGTH: 42
<212> TYPE: DNA
<213> ORGANISM: Cricetulus griseus -continued

```
<400> SEQUENCE: 53

gactgaaaga ctttgaaaga gatgggaggc catcacattg tg                42


<210> SEQ ID NO 54
<211> LENGTH: 55
<212> TYPE: DNA
<213> ORGANISM: Cricetulus griseus

<400> SEQUENCE: 54

gactgaaaga cttgtttgag atgtcatgaa agagatggga ggccatcaca ttgtg  55


<210> SEQ ID NO 55
<211> LENGTH: 55
<212> TYPE: DNA
<213> ORGANISM: Cricetulus griseus

<400> SEQUENCE: 55

gactgaaaga cttgcttgag atgtcatgaa agagatggga ggccatcaca ttgtg  55


<210> SEQ ID NO 56
<211> LENGTH: 55
<212> TYPE: DNA
<213> ORGANISM: Cricetulus griseus

<400> SEQUENCE: 56

gactgaaaga cttgcctgag atgtcatgaa agagatggga ggccatcaca ttgtg  55


<210> SEQ ID NO 57
<211> LENGTH: 31
<212> TYPE: DNA
<213> ORGANISM: Homo sapiens

<400> SEQUENCE: 57

ggcctgagtc cgagcagaag aagaagggct c                            31


<210> SEQ ID NO 58
<211> LENGTH: 31
<212> TYPE: DNA
<213> ORGANISM: Homo sapiens

<400> SEQUENCE: 58

gacaagagtc taagcagaag aagaagagag c                            31


<210> SEQ ID NO 59
<211> LENGTH: 31
<212> TYPE: DNA
<213> ORGANISM: Homo sapiens

<400> SEQUENCE: 59

atgaggaggc cgagcagaag aaagacggcg a                            31


<210> SEQ ID NO 60
<211> LENGTH: 31
<212> TYPE: DNA
<213> ORGANISM: Homo sapiens

<400> SEQUENCE: 60

gacctgagtc ctagcaggag aagaagaggc a                            31
```